United States Patent
Zhang et al.

(10) Patent No.: US 10,273,220 B2
(45) Date of Patent: Apr. 30, 2019

(54) **DERIVATIVE OF *INULA LINEARIIFOLIA* LACTONE A**

(71) Applicant: SHANXI ZHENDONG LEADING BIOTECHNOLOGY CO., LTD., Shanxi (CN)

(72) Inventors: Weidong Zhang, Shanxi (CN); Qingyan Sun, Shanxi (CN); Minghua Li, Shanxi (CN); Baohua Yang, Shanxi (CN)

(73) Assignee: Shanxi Zhendong Leading Biotechnology Co., Ltd., New Taipei (TW)

( * ) Notice: Subject to any disclaimer, the term of this patent is extended or adjusted under 35 U.S.C. 154(b) by 0 days.

(21) Appl. No.: 15/755,558

(22) PCT Filed: Aug. 31, 2016

(86) PCT No.: PCT/CN2016/097481
§ 371 (c)(1),
(2) Date: Feb. 27, 2018

(87) PCT Pub. No.: WO2017/036392
PCT Pub. Date: Mar. 9, 2017

(65) Prior Publication Data
US 2018/0251440 A1    Sep. 6, 2018

(30) Foreign Application Priority Data

Aug. 31, 2015  (CN) .......................... 2015 1 0549327

(51) Int. Cl.
| | |
|---|---|
| *C07D 307/93* | (2006.01) |
| *C07D 307/937* | (2006.01) |
| *A61K 31/365* | (2006.01) |
| *A61P 25/00* | (2006.01) |

(52) U.S. Cl.
CPC .......... *C07D 307/93* (2013.01); *A61K 31/365* (2013.01); *A61P 25/00* (2018.01)

(58) Field of Classification Search
CPC ......................... C07D 307/93; C07D 307/937
See application file for complete search history.

(56) References Cited

U.S. PATENT DOCUMENTS

| 9,278,948 B2 * | 3/2016 | Zhang | ............... A61K 9/19 |
| 9,303,006 B2 * | 4/2016 | Zhang | ............... C07D 307/93 |
| 2015/0105458 A1 * | 4/2015 | Zhang | ............... A61K 9/19 |
| | | | 514/468 |

FOREIGN PATENT DOCUMENTS

| WO | WO-2013188996 A1 * | 12/2013 | ........... A61K 31/365 |
| WO | WO-2013188999 A1 * | 12/2013 | ............... A61K 9/19 |

* cited by examiner

*Primary Examiner* — Nyeemah A Grazier
(74) *Attorney, Agent, or Firm* — Wang Law Firm, Inc.

(57) ABSTRACT

A derivative of *inula lineariifolia* lactone A, and in particular, a dimethylamine 4-O-acetyl *inula lineariifolia* lactone A or a salt thereof, preparation of same, and an application of same in preparation of medicine for treating multiple sclerosis. The dimethylamine 4-O-acetyl *inula lineariifolia* lactone A compound is represented by formula I:

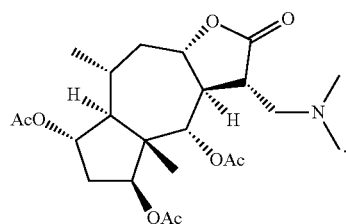

19 Claims, 8 Drawing Sheets

DERIVATIVE OF *INULA LINEARIIFOLIA* LACTONE A

BACKGROUND OF THE INVENTION

Technical Field

The present invention is involved in medicinal chemistry, related to dimethylamine 4-O-acetyl *inula lineariifolia* lactone A or its salts and the application thereof in preparation of medicine, and especially related to dimethylamine 4-O-acetyl *inula lineariifolia* lactone A or its salts, preparation of the same, and an application thereof in preparation of medicine for treating multiple sclerosis.

Technical Background

Since it is first proposed by the French doctor Charcot in 1868, multiple sclerosis (MS) is a disease that still extremely difficult to treat in the world. It is a chronic, autoimmune disease that causes physical disabilities by destroying myelin in the brain, spinal cord and optic nerve which is a protective layer for nerve fiber, and affects normal nerve transmission. Due to its high relapse and disability rate, chronic course and tendency to be developed in young people, usually falling ill in thirty years old, MS has become one of common and important nervous system diseases that extremely affect the productivity and the life quality of young people. It also makes the country and government have a great burden, restricting the development of society and economy.

No curative therapies for MS are currently available and it is lack of satisfactory therapeutic drug. Glucocorticoids are mainly given in the acute phase, and the main therapeutic agents for relapse-remission include interferon-γ, glatiramer acetate and the natalizumab monoclonal antibody. Severe patients can also consider autologous stem cell transplantation. Hormone therapy in western medicine can relieve symptoms of acute phase, but the toxic side effect is obvious, and thus it is not recommended for long-term use; immunomodulators interferon IFN-β, glatiramer acetate (GA) and natalizumab is not only expensive, but long-term use for a single target drug will lead to tolerance. The above drugs should be administrated through intravenous, or injection, and cannot effectively improve the MS recurrence and the fundamental issue of demyelination, that is, no specific treatment for multiple sclerosis, and lacking of satisfactory treatment of drugs. Therefore, there is an urgent need to actively develop oral drugs that can effectively control the recurrence of multiple sclerosis and improve the demyelination, which is of great significance. The traditional Chinese medicine has feature of multiple targets, the role of system regulation, has shown some advantages in the treatment of some rare illness. Therefore, for the complexity and refractory of multiple sclerosis, to explore effective Chinese medicine is also the research direction of scholars.

*Inula lineariifolia* lactone A is extracted from *Inula lineariifolia* Turcz. (syn. *Inula lineariifolia*) and has good therapeutic effect on experimental autoimmune encephalomyelitis (EAE) model on mice that is an ideal animal model for investigation of therapeutic agents for MS. The inventors had applied for patents (An application of *inula lineariifolia* lactone A in the preparation of medicines for multiple sclerosis) in China (CN 20120208157.4). However, further research found that the bioavailability of *inula lineariifolia* lactone A by oral admonition is low. The inventors had modified the structure thereof and a derivative of *inula lineariifolia* lactone A, that is dimethylamine 4-O-acetyl *inula lineariifolia* lactone A, is synthesized. *Inula lineariifolia* lactone A in weak alkaline environment would be hydrolyzed into carboxyl which would react with the 4-hydroxyl to form a new lactone so as to form an isomer of *inula lineariifolia* lactone A which reduce the bioavailability of *inula lineariifolia* lactone A. So the 4-hydroxyl of LA is acetylized first. Further, the α-methylene-γ-lactone structure unit on the structure of *inula lineariifolia* lactone A is unstable, and it could rapidly react with cysteine after entering the blood, and this structure is stable which remarkably decrease the oral bioavailability of *inula lineariifolia* lactone A. The double bond is opened to form a dimethylamine derivative by reacting α-methylene-γ-butyrolactone with dimethylamine. The derivative could slowly eliminate the dimethylamine to form α-methylene-γ-butyrolactone again in neutral and weak alkaline environment and having a pharmacological action.

Experiment results revealed that said derivative and its salt had good effects to treat MS on EAE model, and can be used in drug of MS. Furthermore, they have higher bioavailability than *inula lineariifolia* lactone A by oral administration. All of these implied their potential applications in the treatment of MS.

SUMMARY OF THE INVENTION

The present invention aimed at improving the pharmacokinetics profiles of *inula lineariifolia* lactone A mentioned above and preparing the derivatives of *inula lineariifolia* lactone A and the applications thereof in drug manufacture.

The present invention provides a dimethylamine 4-O-acetyl *inula lineariifolia* lactone A compound represented by compound I:

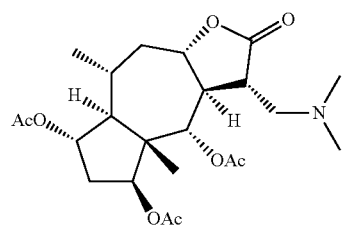

I

The present invention also provides the pharmaceutically acceptable salts of the dimethylamine 4-O-acetyl *inula lineariifolia* lactone A compound, represented by compound II:

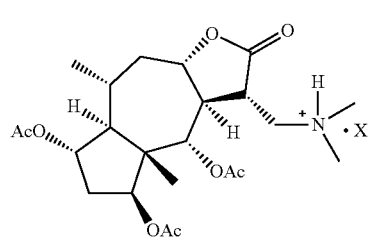

II

The pharmaceutically acceptable salts of the dimethylamine 4-O-acetyl *inula lineariifolia* lactone A compound is synthesized by dimethylamine 4-O-acetyl *inula lineariifolia* lactone and acids (HX).

Wherein, the acids (HX) are hydrochloric acid (HCl), sulfuric acid (H₂SO₄), hydrofluoric acid (HF), hydrobromic acid (HBr), hydroiodic acid (HI), phosphoric acid (H₃PO₄), sulfurous acid (H₂SO₃), nitric acid (HNO₃), carbonic acid (H₂CO₃), boric acid (H₃BO₃), seleninic acid (H₂SeO₃), phosphomolybdic acid (H₃PO₄.12MoO₃), phosphorous acid (H₃PO₃), citric acid, maleic acid, D-malic acid, L-malic acid, DL-malic acid, D-lactic acid, L-lactic acid, DL-lactic acid, oxalic acid, sulphonic acid, benzene sulfonic acid, substituted benzene sulfonic acids, 1-naphthalenesulfonic acid, 2-naphthalenesulfonic acid, phthalic acid, tartaric acid, propandioic acid, succinic acid, fumaric acid, citric acid, orotic acid, benzoic acid or substituted benzoic acids.

The pharmaceutically acceptable salts of dimethylamine 4-O-acetyl LA preferably are dimethylamine 4-O-acetyl *inula lineariifolia* lactone A hydrochloride (compound III), dimethylamine 4-O-acetyl *inula lineariifolia* lactone A fumarate (compound IV), dimethylamine 4-O-acetyl *inula lineariifolia* lactone A nitrate (compound V), dimethylamine 4-O-acetyl *inula lineariifolia* lactone A hydrobromate (compound VI), dimethylamine 4-O-acetyl *inula lineariifolia* lactone A sulfurate (compound VII), dimethylamine 4-O-acetyl *inula lineariifolia* lactone A orotate (compound VIII), dimethylamine 4-O-acetyl *inula lineariifolia* lactone A citrate (compound IX), dimethylamine 4-O-acetyl *inula lineariifolia* lactone A p-toluenesulfonate (compound X) or dimethylamine 4-O-acetyl *inula lineariifolia* lactone A succinate (compound XI), and the most preferably are dimethylamine 4-O-acetyl *inula lineariifolia* lactone A hydrochloride (compound III) and dimethylamine 4-O-acetyl *inula lineariifolia* lactone A fumarate (compound IV).

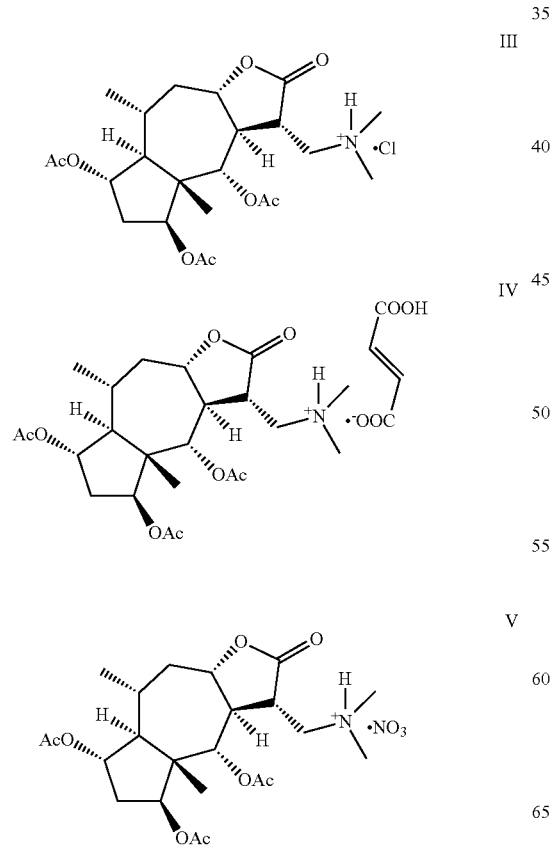

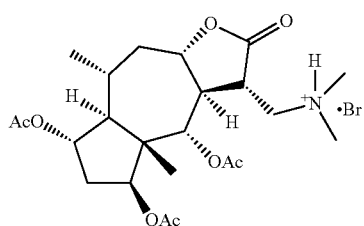

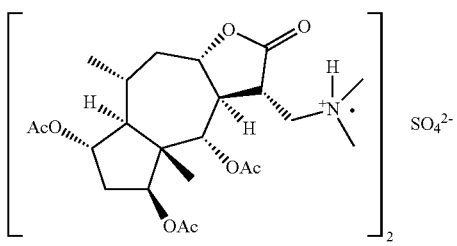

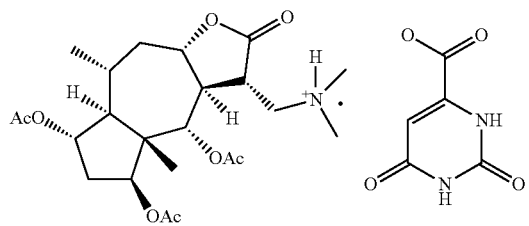

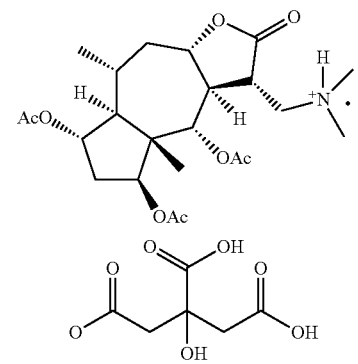

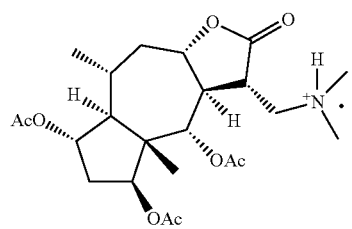

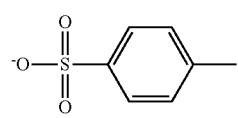

-continued

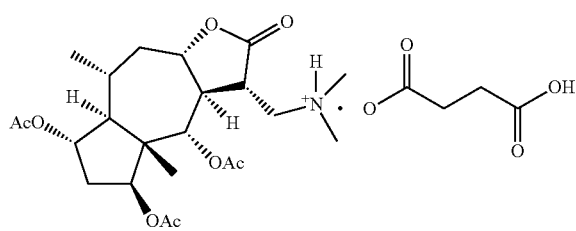

XI

The present invention further provides the preparation methods of the dimethylamine 4-O-acetyl *inula lineariifolia* lactone A compound and its pharmaceutically acceptable salts.

I. The processes to prepare the 4-O-acetyl *inula lineariifolia* lactone A compound, comprising the following steps of:

(1) adding an organic solvent to dissolve *inula lineariifolia* lactone A, a base and acetic anhydride ($Ac_2O$) in a reaction container, stirring at 0-50° C. for 12-24 hours, TLC monitoring the reaction until the reaction material is consumed completely and then quenched by water, and retaining an organic layer;

(2) extracting the organic layer with water several times until a reaction product 4-O-acetyl *inula lineariifolia* lactone A in the organic layer is pure without other impurities by TLC monitoring, discarding an aqueous layer, washing the organic layer with saturated brine, drying with anhydrous sodium sulfate ($Na_2SO_4$), and concentrating to $\frac{1}{10}$-$\frac{1}{20}$ of an original volume under reduced pressure 0.01-0.1 MPa at 20-80° C.;

(3) purifying a concentrated solution by silica-gel column chromatography with gradient elution using petroleum ether (PE)/ethyl acetate (EA) 15:1-5:1 to obtain 4-O-acetyl *inula lineariifolia* lactone A, monitored by TLC; and its reaction equation being shown below:

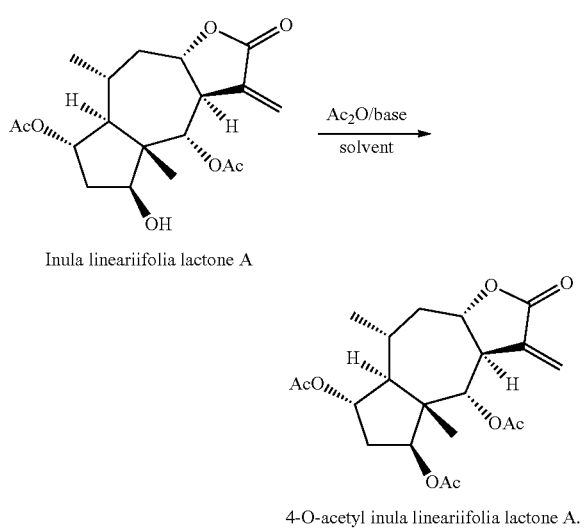

(4) adding an organic solvent to dissolve the 4-O-acetyl *inula lineariifolia* lactone A and dimethylamine hydrochloride ($CH_3NHCH_3 \cdot HCl$) in a reaction container disposed in a cooling tank at −20 to 0° C., slowly adding a base, then slowly increasing a temperature of the reaction mixture to room temperature (25-30° C.), and stirring for 2-12 hours, the reaction being monitored by TLC, until the reaction material is consumed completely, evaporating the solvent under reduced pressure 0.01-0.1 MPa at 20-80° C. to obtain a rude product, then adding an organic solvent to dissolve the rude product, extracting with water, discarding an aqueous layer, repeating the same procedure until a reaction product dimethylamino-4-O-acetyl *inula lineariifolia* lactone A in an organic layer is pure without other impurities by TLC monitoring, washing the organic layer with saturated brine, drying with anhydrous sodium sulfate ($Na_2SO_4$), performing silica-gel column chromatography with gradient elution using PE/EA 15:1-1:1, monitored by TLC, collecting eluent including the dimethylamino-4-O-acetyl *inula lineariifolia* lactone A compound (compound I), evaporating the solvent under reduced pressure 0.01-0.1 MPa at 20-80° C. to obtain the compound I; and its reaction equation being shown below:

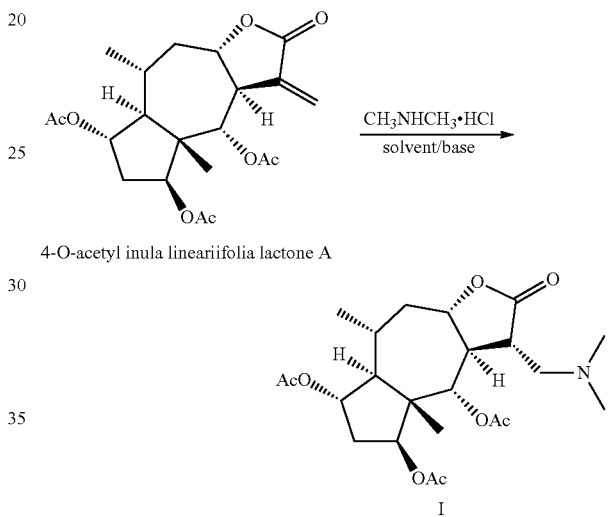

In the step (1) of the method of the present invention, the ratio of dimethylamino-4-O-acetyl LA:the base:acetic anhydride ($Ac_2O$) is 1.0eq:1.0-2.0eq:1.0-2.0eq.

The organic reagent is a reagent insoluble in water, such as one of ethyl acetate, dichloromethane, chloroform, tetrachloromethane, ethyl ether, petroleum ether, n-butyl alcohol, benzene, methylbenzene and tetrahydrofuran, or a mixture thereof, and preferably is dichloromethane.

The base is a low molecular weight trialkyl-substituted amine, such as trimethylamine, triethylamine, tripropylamine or tributylamine, pyridine or substituted pyridine, and preferably is dimethylpyridine.

In the step (4), the ratio of 4-O-acetyl LA:dimethylamine hydrochloride:the base is 1.0eq:1.0-2.0eq:1.0-2.0eq.

The organic solvent is a low molecular weight fatty alcohol, such as one of methanol, ethanol, propanol, isopropanol, dichloromethane, chloroform, tetrachloromethane, ethyl ether, petroleum ether and ethyl acetate, or a mixture thereof, and preferably is ethanol.

The organic reagent is a reagent insoluble in water, such as one of ethyl acetate, dichloromethane, chloroform, tetrachloromethane, ethyl ether, petroleum ether, n-butyl alcohol, benzene, methylbenzene and tetrahydrofuran, or a mixture thereof, and preferably is dichloromethane.

The base is a low molecular weight trialkyl-substituted amine, pyridine or substituted pyridine, the alkyl group is methyl, ethyl, propyl or butyl, and preferably is triethylamine.

II. Preparing the salt of dimethylamino-4-O-acetyl *inula lineariifolia* lactone A compound:

1.0eq of compound I being dissolved in a solvent, and being stirred with 1.0-1.5eq of an acid (HX) at 0-50° C. for 2-24 hours, concentrating under reduced pressure 0.01-0.1 MPa at 20-80° C. to obtaining the salt of compound II, and its reaction equation being shown below:

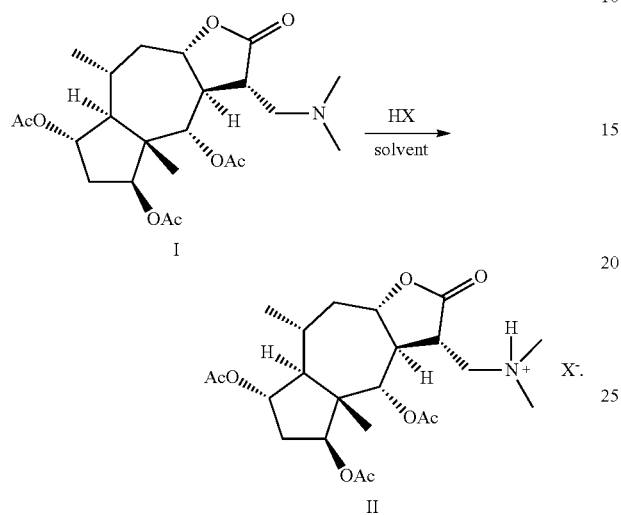

In said method, the ratio of dimethy-4-O-acetyl LA (compound I) and the acid (FIX) is 1.0eq:1.0-1.5eq.

The acid (HX) is hydrochloric acid (HCl), sulfuric acid ($H_2SO_4$), hydrofluoric acid (HF), hydrobromic acid (HBr), hydroiodic acid (HI), phosphoric acid ($H_3PO_4$), sulfurous acid ($H_2SO_3$), nitric acid ($HNO_3$), carbonic acid ($H_2CO_3$), boric acid ($H_3BO_3$), seleninic acid ($H_2SeO_3$), phosphomolybdic acid ($H_3PO_4.12MoO_3$), phosphorous acid ($H_3PO_3$), citric acid, maleic acid, D-malic acid, L-malic acid, DL-malic acid, D-lactic acid, L-lactic acid, DL-lactic acid, oxalic acid, sulphonic acid, benzene sulfonic acid, substituted benzene sulfonic acids, 1-naphthalenesulfonic acid, 2-naphthalenesulfonic acid, phthalic acid, tartaric acid, propandioic acid, butanedioic acid, fumaric acid, citric acid, orotic acid, benzoic acid or substituted benzoic acids, hydrochloric acid, fumaric acid, nitric acid, hydrobromic acid, sulfuric acid, orotic acid, citric acid, p-toluenesulfonic acid, butanedioic acid, and preferably is hydrochloric acid or fumaric acid.

The solvent is a low molecular weight fatty alcohol comprising one of methanol, ethanol, propanol, isopropanol, dichloromethane, chloroform, tetrachloromethane, ethyl ether, petroleum ether and ethyl acetate, or a mixture thereof, and preferably is ethanol.

The purpose of the present invention also provides crystal forms A, D, F, G of dimethylamino-4-O-acetyl *inula lineariifolia* lactone A fumarate (compound IV) and their preparation methods.

The crystal form A of compound IV has the following characteristics:

a powder X-ray diffraction (PXRD) of the crystal form A with values of 2θ, d and relative intensity listed in the following table.

| 2θ | d (Å) | I (Height) % |
|---|---|---|
| 8.101 | 10.9048 | 5.6 |
| 9.72 | 9.092 | 66.5 |
| 10.22 | 8.6484 | 77.4 |
| 11.62 | 7.6093 | 37.7 |
| 12.381 | 7.1435 | 6.8 |
| 14.86 | 5.9568 | 11.7 |
| 15.84 | 5.5903 | 37.8 |
| 16.28 | 5.4402 | 32.3 |
| 17.499 | 5.0639 | 18.4 |
| 19.56 | 4.5347 | 70.2 |
| 20.64 | 4.2998 | 100 |
| 21.081 | 4.2108 | 21.9 |
| 21.819 | 4.07 | 42.6 |
| 23.381 | 3.8016 | 72.4 |
| 24.12 | 3.6866 | 4.3 |
| 24.939 | 3.5674 | 41.5 |
| 25.281 | 3.52 | 40.3 |
| 26.34 | 3.3808 | 7.5 |
| 26.901 | 3.3115 | 11.4 |
| 27.581 | 3.2315 | 16.4 |
| 29.436 | 3.0318 | 4.8 |
| 30.021 | 2.9741 | 7.2 |
| 31.001 | 2.8823 | 23.4 |
| 32.038 | 2.7913 | 6.9 |
| 32.498 | 2.7528 | 2.3 |
| 32.922 | 2.7183 | 3.2 |
| 33.302 | 2.6882 | 10.1 |
| 34.361 | 2.6077 | 3.2 |
| 35.879 | 2.5008 | 5.9 |
| 37.34 | 2.4062 | 5.5 |
| 38.998 | 2.3077 | 4.3 |
| 40.121 | 2.2456 | 7.5 |
| 41.8 | 2.1592 | 7.4 |

The PXRD pattern of the crystal form A is shown in FIG. 1.

First, the compound IV is dissolved in 2 to 5 folds ethyl acetate. Then, 2 to 5 folds n-hexane are added and stirred until a lot of crystals are deposited. The crystals are filtrated and dried under reduced pressure to vacuum at 25-40° C. to obtain the crystal form A of compound IV.

The crystal form D of compound IV has the following characteristics:

A powder X-ray diffraction (PXRD) of the crystal form D with values of 2θ, d and relative intensity listed in the following table:

| 2θ | d (Å) | I (Height) % |
|---|---|---|
| 8.6 | 10.2736 | 100 |
| 9.777 | 9.0388 | 30.8 |
| 10.659 | 8.2929 | 21.5 |
| 11.102 | 7.9633 | 3.7 |
| 13.021 | 6.7936 | 10 |
| 14.64 | 6.0457 | 60.5 |
| 15.039 | 5.8861 | 24 |
| 16.24 | 5.4535 | 35.4 |
| 16.879 | 5.2484 | 20 |
| 17.298 | 5.1221 | 4.7 |
| 17.8 | 4.979 | 5.5 |
| 18.659 | 4.7514 | 13.4 |
| 19.12 | 4.638 | 16.1 |
| 19.619 | 4.5211 | 78.2 |
| 21.418 | 4.1453 | 10.6 |
| 22.3 | 3.9832 | 42.2 |
| 22.801 | 3.8969 | 10.3 |
| 23.266 | 3.82 | 3.8 |
| 23.939 | 3.7141 | 50.4 |
| 24.699 | 3.6015 | 35.6 |
| 25.259 | 3.5229 | 9.7 |
| 25.639 | 3.4716 | 8.3 |
| 26.24 | 3.3935 | 20.8 |
| 27.24 | 3.2711 | 19 |

-continued

| 2θ | d (Å) | I (Height) % |
|---|---|---|
| 27.961 | 3.1883 | 8.8 |
| 28.379 | 3.1423 | 4.2 |
| 28.659 | 3.1123 | 15.7 |
| 28.981 | 3.0784 | 12.7 |
| 29.62 | 3.0135 | 14.2 |
| 29.941 | 2.9818 | 6.5 |
| 30.36 | 2.9416 | 11.2 |
| 30.996 | 2.8827 | 7.4 |
| 31.478 | 2.8397 | 4 |
| 31.861 | 2.8064 | 11.5 |
| 35.799 | 2.5062 | 4.6 |
| 36.646 | 2.4502 | 4.7 |
| 39.882 | 2.2586 | 7.3 |
| 41.057 | 2.1966 | 9.5 |
| 41.9 | 2.1543 | 4.5 |

The PXRD pattern of the crystal form D is shown in FIG. 2.

The preparation method is described as follows:

Compound IV is put into methyl tert-butyl ether (MTBE) containing 0.2% water, and then stirred for 2-5 hours. The solvent is removed by filtration and the solid is dried at 40-60° C. under reduced pressure 0.03-0.1 MPa to vacuum for 4-24 hours to obtain the crystal form D of compound IV.

The crystal form F of compound IV has the following characteristics:

A powder X-ray diffraction (PXRD) of the crystal form F with values of 2θ, d and relative intensity listed in the following table:

| 2θ | d (Å) | I (Height) % |
|---|---|---|
| 8.06 | 10.9609 | 5.4 |
| 9.659 | 9.1493 | 100 |
| 10.08 | 8.7682 | 91.7 |
| 11.5 | 7.6884 | 42.3 |
| 12.139 | 7.2851 | 7.7 |
| 14.642 | 6.0449 | 9.8 |
| 15.639 | 5.6616 | 35.8 |
| 16.2 | 5.4669 | 30 |
| 17.441 | 5.0806 | 15.1 |
| 19.48 | 4.5531 | 73 |
| 20.44 | 4.3413 | 68.1 |
| 20.679 | 4.2916 | 99.4 |
| 21.639 | 4.1034 | 40.1 |
| 23.28 | 3.8177 | 54.9 |
| 24.68 | 3.6043 | 21.8 |
| 25.261 | 3.5227 | 29.8 |
| 25.938 | 3.4322 | 6 |
| 26.52 | 3.3582 | 11.3 |
| 26.938 | 3.3071 | 4.3 |
| 27.482 | 3.2428 | 9.8 |
| 27.958 | 3.1887 | 4.4 |
| 29.201 | 3.0557 | 5.1 |
| 29.918 | 2.9841 | 7.3 |
| 30.442 | 2.9339 | 8.6 |
| 30.839 | 2.8971 | 13.4 |
| 31.657 | 2.824 | 4.7 |
| 33.3 | 2.6884 | 6.2 |
| 34.341 | 2.6092 | 2.6 |
| 35.02 | 2.5601 | 4.1 |
| 35.778 | 2.5076 | 4.3 |

The PXRD pattern of the crystal form F is shown in FIG. 3.

The preparation method is described as follows:

Compound IV is dissolved in 1 to 2 folds methanol. Then, 2 to 5 folds ether are added and stirred until a lot of crystals are deposited. The crystals are filtrated and dried in vacuum at 25-40° C. under 0.03-0.1 MPa to obtain the crystal form F of compound IV.

The crystal form G of compound IV has the following characteristics:

A powder X-ray diffraction (PXRD) of the crystal form G with values of 2θ, d and relative intensity listed in the following table:

| 2θ | d (Å) | I (Height) % |
|---|---|---|
| 8.567 | 10.31279 | 100.0 |
| 7.931 | 9.08148 | 17.0 |
| 10.849 | 8.14803 | 16.7 |
| 11.163 | 7.92006 | 193.4 |
| 12.452 | 7.10295 | 0.8 |
| 12.865 | 6.87584 | 2.7 |
| 13.115 | 6.74542 | 1.0 |
| 14.413 | 6.14053 | 17.9 |
| 14.869 | 5.95311 | 20.0 |
| 15.128 | 5.85184 | 3.2 |
| 16.225 | 5.45870 | 9.0 |
| 17.268 | 5.13128 | 13.8 |
| 18.761 | 4.72601 | 26.8 |
| 19.661 | 4.51181 | 6.0 |
| 21.872 | 4.06030 | 20.3 |
| 22.059 | 4.02635 | 22.8 |
| 23.059 | 3.85401 | 1.9 |
| 23.631 | 3.73193 | 3.0 |
| 24.014 | 3.70281 | 2.1 |
| 24.809 | 3.58595 | 3.0 |
| 25.401 | 3.50361 | 13.1 |
| 25.830 | 3.44652 | 6.9 |
| 26.245 | 3.39285 | 7.6 |
| 27.267 | 3.26804 | 2.5 |
| 28.160 | 3.16634 | 5.4 |
| 29.131 | 3.06300 | 5.0 |
| 30.138 | 2.96286 | 3.8 |
| 30.797 | 2.90094 | 4.1 |
| 32.824 | 2.72631 | 1.0 |
| 33.257 | 2.69179 | 0.6 |
| 34.654 | 2.58642 | 1.6 |
| 36.124 | 2.48445 | 1.2 |
| 38.027 | 2.36438 | 1.0 |
| 38.503 | 2.33628 | 1.0 |
| 38.942 | 2.31091 | 1.0 |

The PXRD pattern of the crystal form G is shown in FIG. 4.

The preparation method is described as follows:

Compound I is dissolved in 2 folds ethanol, then added with equivalent fumaric acid with stirring. The mixture is stirred for 0.5-2 hours and then added with 1 to 2 folds MTBE to separate out crystals. The crystals are filtrated, drip washed by MTBE and dried at 25-40° C. in vacuum to obtain the crystal form G of compound IV.

The further purpose of the present invention provides the application of dimethylamine 4-O-acetyl-sevoflurane A compound and pharmaceutically acceptable salts thereof in preparation of medicine for treating multiple sclerosis.

The inventors used an animal model of EAE to conduct EAE animal model efficacy test of dimethylamine 4-O-acetyl-secloflorate A (compound I). Experimental autoimmune encephalomyelitis (EAE) is an ideal animal model and usually use in researching the mechanisms of immune activation and immunosuppression. The effect of compound I in the EAE model has the result that compound I and fumarate IV are administered by intragastric administration respectively, which could significantly reduce the incidence of EAE (see FIG. 5, FIG. 6). EAE mice in the model group having inflammatory cell of brain tissue infiltration, loosely tissue and the boundary is unclear in the blood vessels and tissues; in the administration group, the inflammatory cell decreased and the blood vessels and tissues returned to their normal levels (FIG. 7 and FIG. 8). Intragastric administration of compound I and fumarate IV is better for preventing the process of EAE. The result indicated that compound 1 or its salt could be used in the preparation of medicine for the treatment of MS.

The drugs prepared for MS mentioned in the present invention are pharmaceutical compositions made of dimethylamino-4-O-acetyl *inula lineariifolia* lactone A (compound I) or its salts (compound II) as active ingredient, combined with medicinal carriers.

The pharmaceutical compositions are tablets, dispersible tablets, lozenge, mouth collapse tablets, retard tablets, capsules, soft capsules, dropping pills, granules, injections, powder injections, aerosols and so on.

The dimethylamine 4-O-acetyl *inula lineariifolia* lactone A compound of the present invention has higher bioavailability than *inula lineariifolia* lactone A. The present invention provides new potential clinical treatments for MS and has larger social benefit.

DESCRIPTION OF THE PREFERRED EMBODIMENTS

Figure 1:
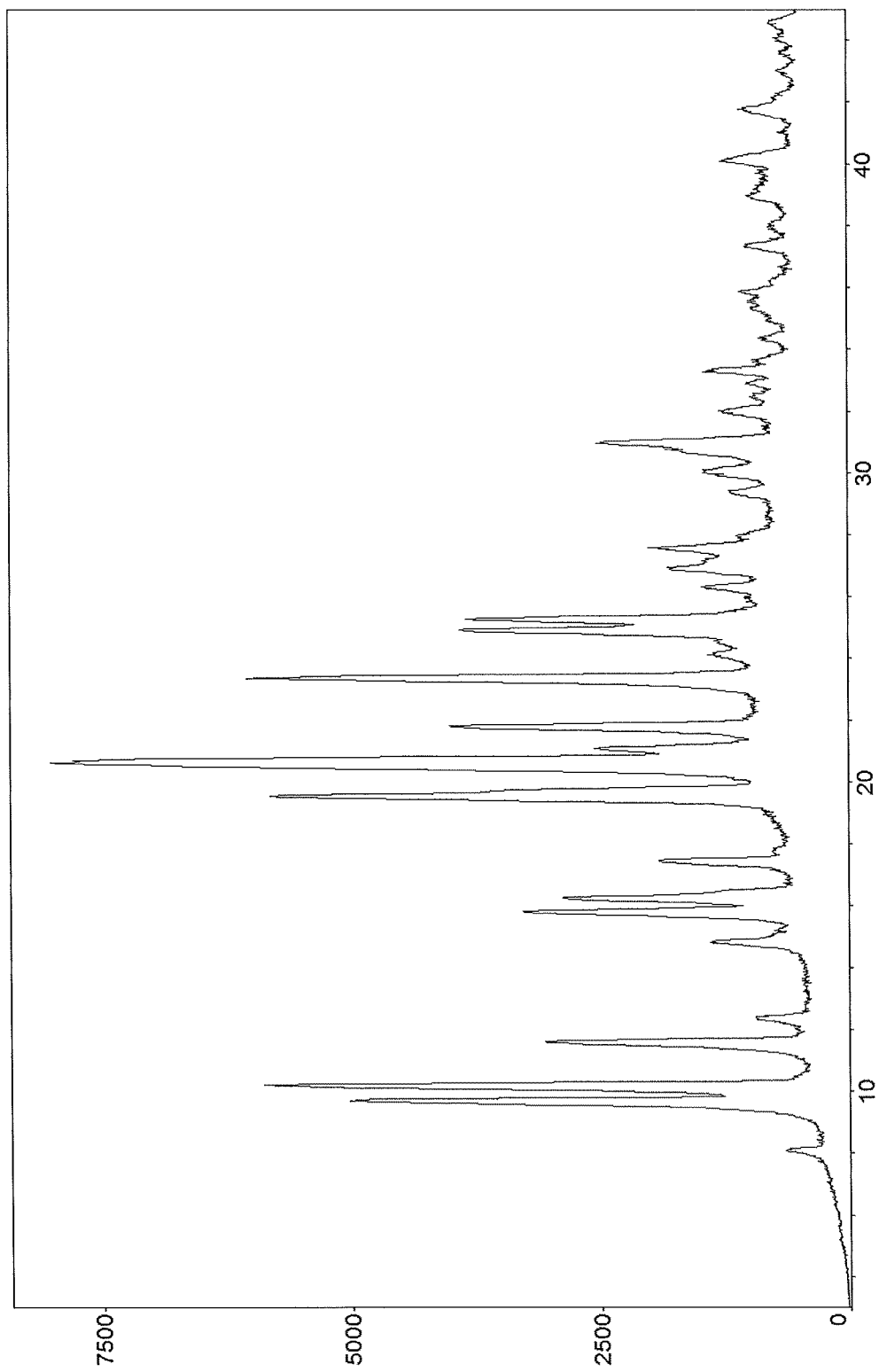
FIG. 1 is a PXRD pattern of compound IV in crystal form A.

Materials and reagents used in the following examples are purchased from the market.

Embodiment 1: Preparation of *Inula lineariifolia* Lactone A (LA)

Shivering the dried whole grass of *inula lineariifolia* 50 kg, then extracted with 750 L ethanol (80-95% V/V) for two times, 2 hours each time. The extracted fluid was combined and condensed into liquid extract with a density of 1 g raw material per milliliter extract under reduced pressure. The liquid extract was diluted with 50 L water, then extracted 5 times with 50 L petroleum ether each time to obtain the petroleum ether extract that was condensed and further purified by silica gel column chromatography. The silica gel column was eluted with gradient petroleum ether/ethyl acetate (100:0-1:1). The elution was detected by thin-layer chromatography and the portion containing LA was collected and condensed to apply on C18 reverse phase column chromatography for further purification. The C18 column was eluted with gradient methanol/water (50:100-70:100) and the fractions containing only LA was collected and condensed to obtain 45.3 g pure LA.

The compound was identified first by mass spectrometry to obtain the molecular weight of 366 and formula of $C_{19}H_{28}O_7$, then by 1 H-NMR and 13C-NMR, as well as two-dimensional NMR to analysis the structure. The data were consistent with those of LA.

Embodiment 2: Preparation of 4-O-acetyl-L A

LA (10.0 g, 0.027 mol, 1.0 eq), 2,6-Dimethylpyridine (DMAP) (4.0 g, 0.033 mol, 1.2 eq) and acetic anhydride ($Ac_2O$)(3.34 g, 0.033 mol, 1.2 eq) were dissolved in 200 mL dichloromethane, then stirred in a 500 mL round-bottom flask at 0-50° C. for 12 hours. The reaction was monitored by TLC, until the reaction material was consumed completely. The reaction was quenched by 200 mL water, and discards the aqueous layer. The organic layer was extracted with 100 mL water several times until the reaction product 4-O-acetyl LA in the organic phase was pure without DMPA (monitored by TLC). The organic layer was washed with saturated brine and dried with anhydrous sodium sulfate. Then the solvent was condensed—under reduced pressure (0.01-0.1 MPa) at 40° C.

The concentrated solution was purified by silica-gel column chromatography, gradient eluted with PE/EA 15:1-5:1 to obtain 4-O-acetyl LA (10.5 g, 0.026 mol) with a yield of 94%. The measurement confirmed the product:

$^1$H NMR (500 MHz, Chloroform-d) δ 6.14 (dt, J=3.8, 1.1 Hz, 1H), 5.51 (dd, J=3.2, 1.6 Hz, 1H), 5.26-5.19 (m, 1H), 5.15 (dt, J=8.6, 1.6 Hz, 1H), 4.91 (t, J=7.8 Hz, 1H), 4.49-4.42 (m, 1H), 3.01-2.93 (m, 1H), 2.43-2.36 (m, 1H), 2.08-2.06 (m, 3H), 2.03 (q, J=1.2 Hz, 3H), 2.00-1.93 (m, 6H), 1.89 (dd, J=12.0, 5.9 Hz, 1H), 1.48-1.38 (m, 1H), 1.08 (d, J=1.2 Hz, 3H), 0.97 (dd, J=6.4, 1.4 Hz, 3H); 13C NMR (125 MHz, Chloroform-d) δ 170.7, 170.3, 169.7, 168.9, 137.9, 121.2, 76.1, 75.0, 73.7, 73.6, 52.4, 50.3, 50.3, 43.9, 34.2, 29.8, 21.2, 21.1, 20.9, 20.3, 17.3.

Embodiment 3: Preparation of Dimethyl-4-O-Acetyl LA (Compound I)

Abovementioned 4-O-acetyl LA (10.0 g, 0.024 mol, 1.0 eq) and dimethylamine hydrochloride (CH3NHCH3.HCl) (3.0 g, 0.037 mol, 1.5 eq) were dissolved in 200 mL ethanol, then stirred in a 500 mL reaction flask at cooling tank with 0° C. Triethylamine (5.1 mL, 0.037 mol, 1.5 eq) was added to the mixture slowly and carefully, then the reaction mixture was warmed up to room temperature (25-30° C.) and stirred for 4 hours, the reaction was monitored by TLC. Until the reaction material was consumed completely, the solvent was evaporated under reduced pressure (0.01-0.1 MPa) at 40° C. to obtain the rude product. Then the rude product was dissolved in 200 mL dichloromethane, extracted with 100 mL water then discarded the aqueous layer, the same procedure was repeated several times until the organic layer was pure without dimethylamine hydrochloride (monitored by TLC). The organic layer is washed with saturated brine and dried with anhydrous sodium sulfate. The concentrated solution was monitored by TLC, purified by silica-gel column chromatography, gradient eluted with PE/EA 15:1-1:1 to obtain the solution of dimethylamino-4-O-acetyl LA (10.0 g, 0.022 mol) with a yield of 90%.

¹H-NMR (500 MHz, Chloroform-d) δ 5.27 (dd, J=10.7, 8.6 Hz, 1H), 5.04 (d, J=9.5 Hz, 1H), 4.92 (ddd, J=9.2, 6.8, 2.1 Hz, 1H), 4.40 (ddd, J=11.7, 10.1, 2.8 Hz, 1H), 2.69-2.61 (m, 2H), 2.53 (dd, J=9.3, 6.5 Hz, 1H), 2.45 (dd, J=13.1, 5.3 Hz, 1H), 2.36 (ddd, J=13.2, 4.5, 2.8 Hz, 1H), 2.18 (s, 6H), 2.08-2.05 (m, 1H), 2.03 (s, 4H), 2.01 (s, 3H), 1.97 (s, 3H), 1.96-1.87 (m, 2H), 1.40 (dt, J=13.1, 11.9 Hz, 1H), 1.12 (s, 3H), 0.97 (d, J=6.5 Hz, 3H); 13C-NMR (125 MHz, Chloroform-d) δ 176.6, 170.4, 170.3, 169.5, 77.2, 76.2, 76.1, 74.9, 74.3, 57.4, 50.0, 50.0, 48.7, 46.9, 46.3, 43.8, 34.3, 29.4, 21.1, 21.1, 20.8, 20.16, 18.5.

Embodiment 4: Preparation of Compound III compound I (10.0 g, 0.022 mol) obtained through embodiment 3 was dissolved in 200 mL anhydrous methanol, then stirred at room temperature (25-30° C.) for half an hour after 500 mL standard HCl gas flowing in. The solution was evaporated under reduced pressure (0.01-0.1 MPa) at 40° C. to obtain the hydrochloride (compound III) (10.0 g, 0.022 mol).

1H-NMR (500 MHz, D2O) δ 5.24-5.16 (m, 2H), 5.02 (td, J=6.8, 4.5 Hz, 1H), 4.93-4.84 (m, 1H), 3.68 (dd, J=13.4, 11.5 Hz, 1H), 3.45 (td, J=11.4, 4.0 Hz, 1H), 3.37 (s, 1H), 2.99 (dd, J=13.3, 4.0 Hz, 7H), 2.74 (d, J=11.5 Hz, 1H), 2.44-2.36 (m, 1H), 2.19 (s, 3H), 2.16 (d, J=6.7 Hz, 1H), 2.14 (d, J=1.0 Hz, 3H), 2.13-2.07 (m, 2H), 2.08 (s, 3H), 1.53 (q, J=12.2 Hz, 1H), 1.22 (s, 3H), 0.99 (d, J=6.5 Hz, 3H); 13C NMR (125 MHz, D2O) δ 177.20, 172.43, 171.0 (2×C), 79.2, 77.2 (2×C), 75.9, 75.2, 57.4, 49.8, 49.8 (2×C), 49.4, 42.3, 41.9, 33.5, 28.5, 20.9, 20.57, 20.6, 19.5, 17.4.

Embodiment 5: Preparation of Compound IV

Compound I (10.0 g, 0.022 mol) obtained through embodiment 1 was dissolved in 200 mL anhydrous methanol, added analytical fumaric acid (2.6 g, 0.022 mol), and then stirred at room temperature (25° C.) for half an hour. The solution was evaporated under reduced pressure (0.03-0.1 MPa) at 40° C. to obtain the fumarate (compound IV) (12.6 g, 0.022 mol).

¹H-NMR (500 MHz, D2O) δ 6.72 (d, J=1.1 Hz, 2H), 5.23-5.16 (m, 2H), 5.00 (td, J=6.8, 4.5 Hz, 1H), 4.90-4.84 (m, 1H), 3.66 (dd, J=13.4, 11.5 Hz, 1H), 3.44 (td, J=11.4, 4.0 Hz, 1H), 3.36 (s, 1H), 2.98 (dd, J=13.3, 4.0 Hz, 7H), 2.72 (d, J=11.5 Hz, 1H), 2.42-2.36 (m, 1H), 2.17 (s, 3H), 2.14 (d, J=6.7 Hz, 1H), 2.12 (d, J=1.0 Hz, 3H), 2.11-2.07 (m, 2H), 2.06 (s, 3H), 1.50 (q, J=12.2 Hz, 1H), 1.20 (s, 3H), 0.98 (d, J=6.5 Hz, 3H); 13C-NMR (125 MHz, D2O) δ 177.18, 173.61, 173.50, 172.41, 170.9 (2×C), 134.8 (2×C), 79.0, 77.0 (2×C), 75.7, 75.0, 57.2, 49.6, 49.6 (2×C), 49.2, 42.1, 41.7, 33.3, 28.3, 20.7, 20.5, 20.4, 19.3, 17.2.

Embodiment 6: Preparation of Compound V

Compound I (10.00 mg, 0.22 m mol) obtained through embodiment 1 was dissolved in 10 mL ethyl acetate, added 1% nitric acid (1 mL, 0.22 mmol), and then stirred at room temperature (25° C.) for half an hour. The solution was evaporated under reduced pressure (0.03-0.1 MPa) at 40° C. to remove ethyl acetate and obtain the nitrate (compound V) (113 mg, 0.22 mmol).

¹H NMR (400 MHz, (CD3)2SO) 8.92 (s, 1H), 5.03-5.10 (m, 2H), 4.89-4.94 (m, 1H), 4.65-4.71 (m, 1H), 3.46-3.52 (m, 1H), 3.36-3.39 (m, 1H), 2.81-2.87 (m, 4H), 2.73 (s, 3H), 2.63 (q, J=10.0 Hz, 1H), 2.18-2.21 (m, 1H), 2.05 (s, 3H), 2.02 (s, 3H), 1.83-1.99 (m, 7H), 1.41 (q, J=11.6 Hz, 1H), 1.09 (s, 3H), 0.89 (d, J=5.6 Hz, 3H).

Embodiment 7: Preparation of Compound VI

Compound I (10.00 mg, 0.22 m mol) obtained through embodiment 1 was dissolved in 10 mL ethyl acetate, added 1 mol/L hydrobromic acid (0.22 mL, 0.22 mmol), and then stirred at 25° C. for half an hour. The solution was evaporated under reduced pressure (0.03-0.1 MPa) at 40° C. to removed ethyl acetate and obtain the hydrobromate (compound VI) (117 mg, 0.22 mmol).

¹H NMR (400 MHz, (CD3)2SO) 8.96 (br, 1H), 5.01-5.09 (m, 2H), 4.91-4.94 (m, 1H), 4.66-4.72 (m, 1H), 3.32-3.40 (m, 2H), 2.59-2.85 (m, 8H), 2.18-2.21 (m, 1H), 2.05 (s, 3H), 2.02 (s, 3H), 1.83-1.99 (m, 7H), 1.41 (q, J=12.0 Hz, 1H), 1.10 (s, 3H), 0.89 (d, J=5.6 Hz, 3H).

Embodiment 8: Preparation of Compound VII

Compound I (10.00 mg, 0.22 m mol) obtained through embodiment 1 was dissolved in 10 mL ethyl acetate, added 1% sulfuric acid (0.6 mL, 0.11 mmol), and then stirred at 25° C. for half an hour. The solution was evaporated under reduced pressure (0.03-0.1 MPa) at 40° C. to removed ethyl acetate and obtain the sulfurate (compound VII) (110 mg, 0.22 mmol).

¹H NMR (400 MHz, (CD3)2SO) 8.92 (s, 1H), 5.01-5.09 (m, 2H), 4.91-4.94 (m, 1H), 4.66-4.72 (m, 1H), 4.52 (br, 1H), 3.47-3.53 (m, 1H), 3.34-3.40 (m, 1H), 2.79-2.88 (m, 4H), 2.73 (s, 3H), 2.63 (q, J=10.0 Hz, 1H), 2.18-2.21 (m, 1H), 2.05 (s, 3H), 2.02 (s, 3H), 1.83-1.99 (m, 7H), 1.41 (q, J=11.6 Hz, 1H), 1.10 (s, 3H), 0.89 (d, J=5.6 Hz, 3H).

Embodiment 9: Preparation of Compound VIII

Compound I (10.00 mg, 0.22 m mol) obtained through embodiment 1 was dissolved in 10 mL ethyl acetate, added orotic acid (35 mg, 0.22 mmol), and then stirred at 25° C. for half an hour. The solution was evaporated under reduced pressure (0.03-0.1 MPa) at 40° C. to removed ethyl acetate and obtain the orotate (compound VII) (135 mg, 0.22 mmol).

¹H NMR (400 MHz, (CD3)2SO) 11.05 (s, 1H), 9.93 (s, 1H), 5.83 (s, 1H), 5.02-5.07 (m, 2H), 4.90-4.93 (m, 1H), 4.61-4.67 (m, 1H), 3.68 (br, 1H), 3.06-3.14 (m, 2H), 2.79 (d, J=11.6 Hz, 1H), 2.65 (q, J=10.0 Hz, 1H), 2.56 (s, 6H), 2.18-2.22 (m, 1H), 2.02 (s, 3H), 2.00 (s, 3H), 1.82-1.98 (m, 7H), 1.38 (q, J=12.0 Hz, 1H), 1.09 (s, 3H), 0.88 (d, J=6.0 Hz, 3H).

Embodiment 10: Preparation of Compound IX

Compound I (10.00 mg, 0.22 m mol) obtained through embodiment 1 was dissolved in 10 mL ethyl acetate, added citric acid (43 mg, 0.22 mmol), and then stirred at 25° C. for half an hour. The solution was evaporated under reduced pressure (0.03-0.1 MPa) at 40° C. to removed ethyl acetate and obtain the citrate (compound IX) (143 mg, 0.22 mmol).

1H NMR (400 MHz, (CD3)2SO) of compound IX: 11.44 (br, 1H), 8.33 (br, 1H), 5.97 (d, J=3.2 Hz, 1H), 5.35 (d, J=2.8 Hz, 1H), 5.01-5.10 (m, 2H), 4.91-4.95 (m, 1H), 4.64-4.70 (m, 1H), 3.22-3.29 (m, 2H), 2.55 (s, 6H), 2.54 (dd, J=31.2, 15.2 Hz, 4H), 2.17-2.22 (m, 1H), 2.11 (s, 2H), 2.03 (s, 3H), 2.02 (s, 3H), 1.91-2.01 (m, 7H), 1.52 (q, J=12.0 Hz, 1H), 1.07 (s, 3H), 0.89 (d, J=6.4 Hz, 3H).

Embodiment 11: Preparation of Compound X

Compound I (10.00 mg, 0.22 m mol) obtained through embodiment 1 was dissolved in 10 mL ethyl acetate, added anhydrous p-toluenesulfonic acid (38 mg, 0.22 mmol), and then stirred at 25° C. for half an hour. The solution was evaporated under reduced pressure (0.03-0.1 MPa) at 40° C. to removed ethyl acetate and obtain the p-toluenesulfonate (compound VII) (138 mg, 0.22 mmol).

1H NMR (400 MHz, (CD3)2SO) 8.92 (s, 1H), 7.49 (d, J=8.0 Hz, 2H), 7.12 (d, J=8.0 Hz, 2H), 5.01-5.09 (m, 2H), 4.91-4.94 (m, 1H), 4.66-4.72 (m, 1H), 3.47-3.53 (m, 1H), 3.33-3.40 (m, 1H), 2.81-2.88 (m, 4H), 2.73 (s, 3H), 2.63 (q, J=10.0 Hz, 1H), 2.29 (s, 3H), 2.17-2.20 (m, 1H), 2.04 (s, 3H), 2.02 (s, 3H), 1.83-1.98 (m, 7H), 1.41 (q, J=11.6 Hz, 1H), 1.09 (s, 3H), 0.88 (d, J=5.6 Hz, 3H).

Embodiment 12: Preparation of Compound XI

Compound I (100 mg, 0.22 m mol) obtained through embodiment 3 was dissolved in 10 mL ethyl acetate, added anhydrous succinic acid (26 mg, 0.22 mmol), and then stirred at 25° C. for half an hour. The solution was evaporated under reduced pressure (0.03-0.1 MPa) at 40° C. to remove ethyl acetate and obtain the succinate (compound VII) (126 mg, 0.22 mmol).

Embodiment 13: Preparation of the Crystal Form A of Compound IV

Compound IV obtained through embodiment 5 is dissolved in 20 mL ethyl acetate. Than 50 mL hexane were added and stirred until a lot of crystals were deposited. The crystals were filtrated and dried under reduced pressure (0.03-0.1 MPa) at 40° C. to obtain the crystal form A of compound IV (8.5 g).

Embodiment 14: Preparation of the Crystal Form D of Compound IV

Compound IV obtained through example 5 was put into 30 mL MTBE (methyl tert-butyl ether), then stirred for 3 hours at 25° C., The solvent was dried at 45° C. under 0.03-0.1 MPa for 4 hours to obtain the crystal form D of compound IV (9.1 g).

Embodiment 15: Preparation of the Crystal Form F of Compound IV

Compound IV obtained through embodiment 5 was dissolved in 20 mL methanol. Then 50 mL ether were added and stirred until a lot of crystals were deposited. The crystals were filtrated and dried at 40° C. under reduced pressure (0.03-0.1 MPa) for 4 hours to obtain the crystal form A (8.9 g).

Embodiment 16: Preparation of the Crystal Form G of Compound IV

Compound I (10. g) was dissolved in 20 mL ethanol, then added with equivalent fumaric acid (2.6 g) when stirring. The mixture was stirred for 2 hours and then added with 20 mL MTBE to separate out crystals. The crystals were filtrated, drip washed by MTBE and dried in vacuum with 25-40° C. for 2 hours to obtain the crystal form G of (10.6 g).

Embodiment 17: Pharmacodynamics Studies of Compound Ion EAE Model

Mice with experimental autoimmune encephalomyelitis (EAE) model is an ideal animal model of multiple sclerosis (MS), often used in the study of the mechanism of immune activation and immunosuppression.

17.1 Induction of EAE Model

C57BL/6 mice (six mice per group, 18-20 g) received a subcutaneous injection of 300 µg/mice MOG 35-55 peptide emulsified in complete Freund's adjuvant containing 400 µg *Mycobacteria tuberculosis*. On Days 0 and 2 post immunization, 200 µl pertussis toxin 500 µg/mice were applied by intraperitoneal injection. The animals are divided into 6 mice per group.

17.2 Compound Dosing

Compound I 45.3 g (prepare from Embodiment 1) was suspended in the 0.5% CMC-Na (carboxymethyl cellulose sodium) and prepare in solution of 3 mg/ml. Applying once a day from day 0 of immunization at a dosage of 30 mg/kg body weight, continuous administration of 30 days.

17.3 The Results

Figure 5:
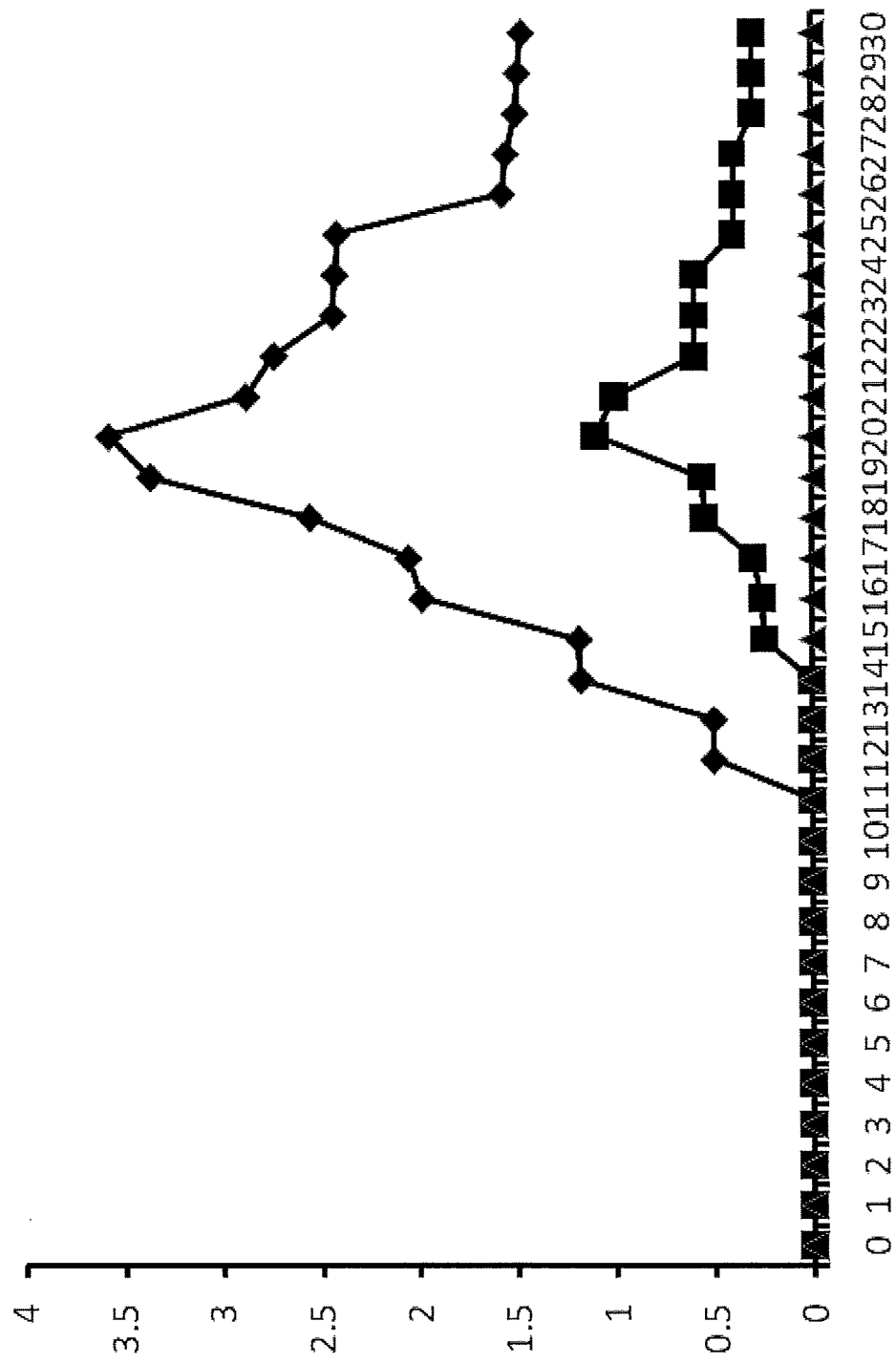
FIG. 5 is variation of EAE score after intragastrically administrated compound I (30 mg/kg). Y-axis is EAE score and X-axis is days after immunization (Three lines from top to bottom represented EAE model treated by vehicle, EAE model treated by compound I and naive, respectively).
Figure 6:
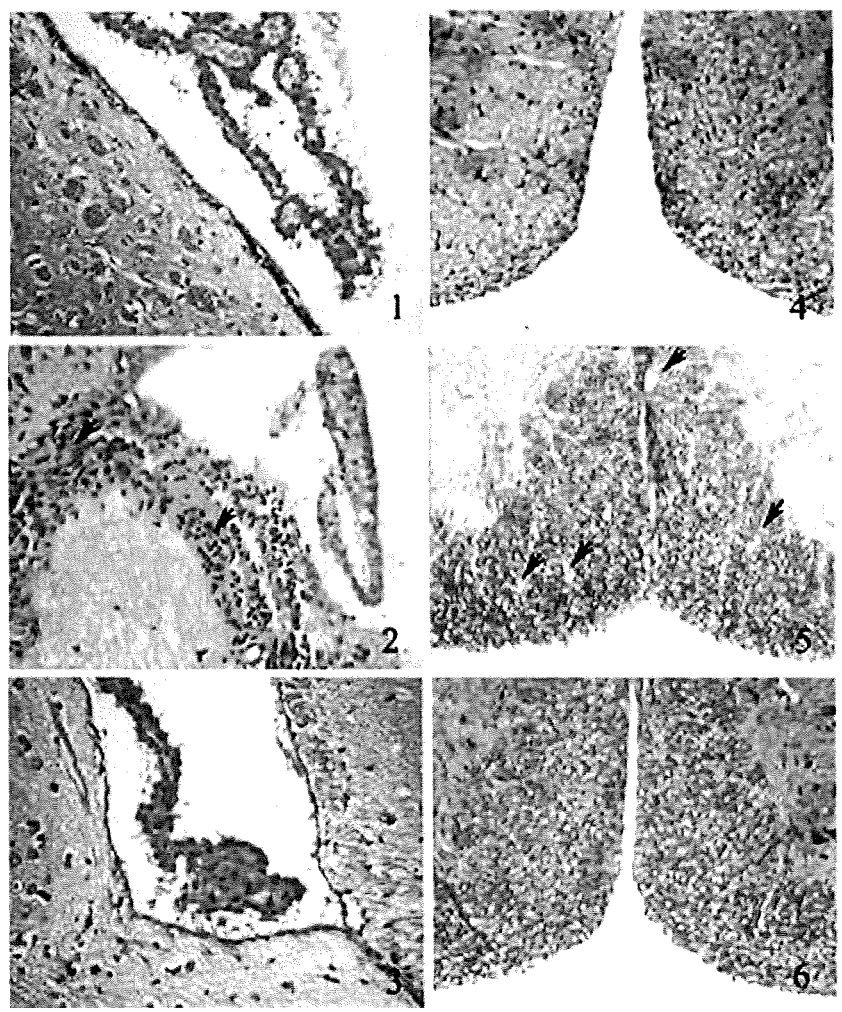
FIG. 6 is variation of EAE score after intragastrically administrated compound IV (15 mg/kg). Y-axis is EAE score and X-axis is days after immunization (Three lines from top to bottom represented EAE model treated by vehicle, EAE model treated by compound IV and naive, respectively).

Compound I (30 mg/kg/day by intragastrically administrated) delayed the onset of EAE, and reduced disease severity (FIG. 5). Mice in EAE model group showed inflammation cells infiltration, the arrangement of the blood vessel and tissue is loose, and the edge is not clear. Mice treated by compound 1 showed the reduced inflammatory cells, the arrangement of the organization basically returned to normal condition. The demyelination of the administration group was significantly reduced (FIG. 6).

The above experiment was repeated 3 times. The results were as same as above mentioned.

17.4 Toxicity

Mice were divided into four groups for each having three males and three females and treated by compound 1 at a single-dose of 200, 600, 1800 and 5400 mg/kg, respectively. Five mice except one male mouse died in the group of 5400 mg/kg. One female mouse died in the group treated at dose of 1800 mg/kg. No obvious toxic reactions were observed in groups treated at dose of 200 and 600 mg/kg. The results indicated that compound 1 had a good safety.

17.5 The Conclusion

Compound 1 (30 mg/kg) ameliorated the course of EAE, which indicated that it might have good effect on MS and have potential in preparation of medicine for treatment of MS.

Embodiment 18: Pharmacodynamics Studies of the Fumarate of Dimethylamine 4-O-Acetyl LA (Compound IV) on EAE Model 18.1 Induction of MOG-EAE and Treatment Protocol The induction method was the same with embodiment 17.

18.2 Compound Dosing

Compound IV, crystal type A was dissolved in injection water to prepare the 1.5 mg/mL solution. Starting from Day 0 post injection at a dosage of 15 mg/kg body weight once a day via oral gavage. Control animals received vehicle orally as sham treatment.

18.3 Results

Figure 7:
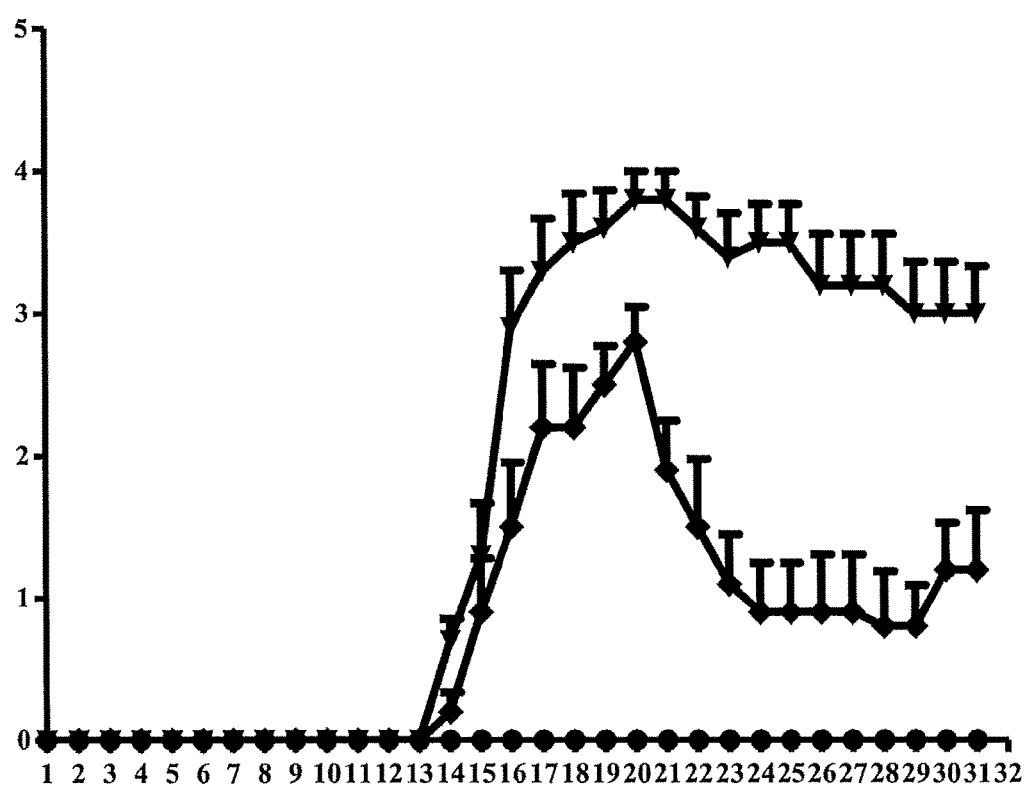
FIG. 7 is H&E analysis of Cervical Spinal Cord (1: naive, 2: EAE model treated by vehicle, 3: model treated by compound I 30 mg/kg) and LFB staining of Cervical Spinal Cord (4: naive, 5: EAE model treated by vehicle, 6: model treated by compound I 30 mg/kg).
Figure 8:
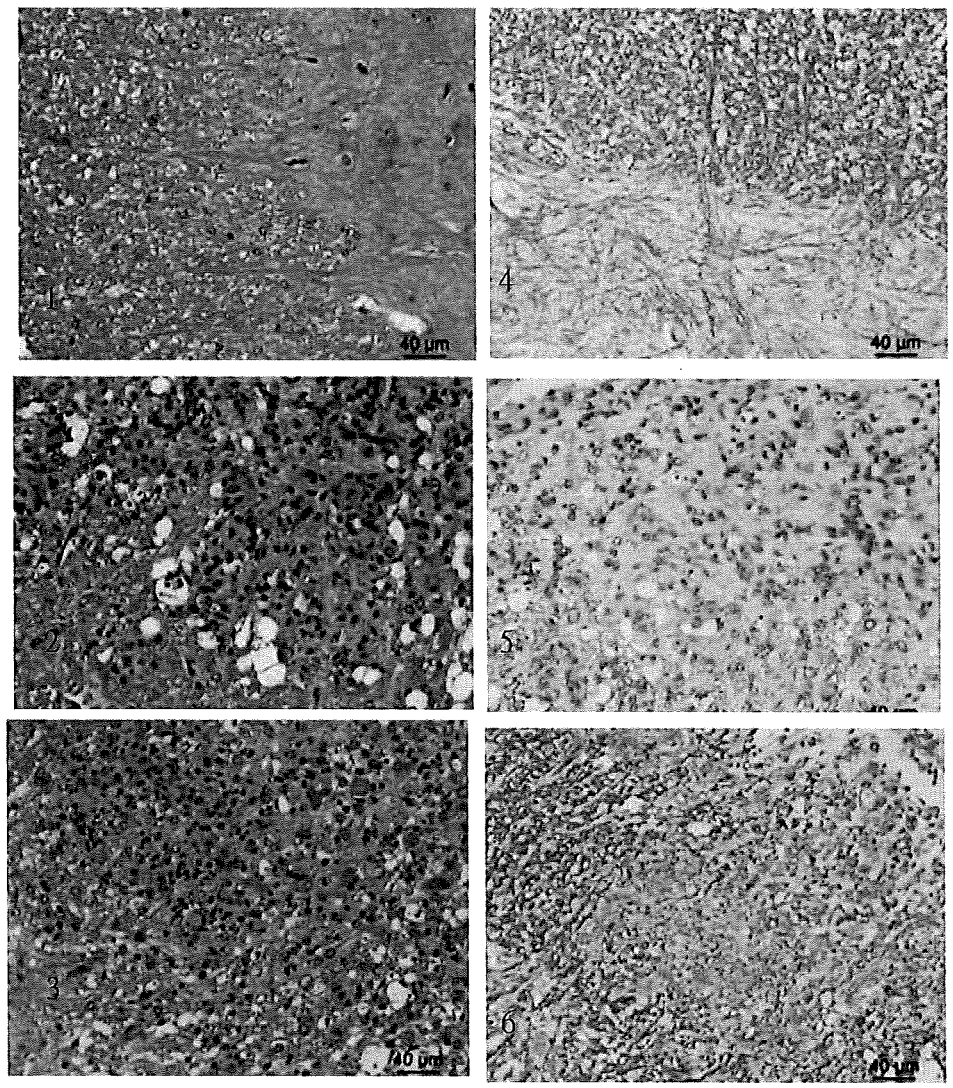
FIG. 8 is H&E analysis of Cervical Spinal Cord (1: naive, 2: EAE model treated by vehicle, 3: model treated by compound IV 15 mg/kg) and LFB staining of Cervical Spinal Cord (4: naive, 5: EAE model treated by vehicle, 6: model treated by compound IV 15 mg/kg).

Compound IV (15 mg/kg once daily) delayed the onset of EAE and reduced disease severity (FIG. 7). Mice in EAE model group showed inflammation cells infiltration, the arrangement of the blood vessel and tissue is loose, and the edge is not clear. Mice treated by compound IV showed the reducing inflammatory cells, the arrangement of the organization basically returned to normal condition and significant lower demyelination comparing to EAE model control (FIG. 8).

18.4 Toxicity of Compound IV

Sprague Dawley rats, each group having 3 males and 3 females were administrated intragastrically daily at 75, 150, 300 mg/kg respectively for 7 consecutive days. No obvious toxic reactions were observed which indicated that compound IV had a good safety.

18.5 Conclusion

Compound IV ameliorated the course of EAE, which indicated that it might have good effect on MS and have potential in preparation of medicine for treatment of MS.

Embodiment 19: Preparation of Tablets

Compound I from Embodiment 1 25 g
Lactose 210 g
Corn starch 60 g
Magnesium stearate 5 g Preparation methods: Mix compound I with lactose and corn starch, wetting with water following with sieving, drying and sieving again, mixing with magnesium stearate and tablet compressing. The final tablet weight was about 300 mg for each containing 25 mg of compound I.

Embodiment 20: Preparation of Injections

Compound III from Embodiment 2 5 g
Glucose 50 g

Preparation methods: Compound III and glucose were dissolved in 100 L of water for injection, then filtered and filled into infusion bottles under sterile conditions. Each bottle had 100 mL solution containing 5 mg compound III.

Embodiment 21: Preparation of Lyophilization Powder for Injection

Compound IV from Embodiment 3 10 g
Mannitol 30 g

Preparation: Compound IV and glucose were dissolved in 2 L of water for injection, then filtered and filled an aliquot of 2 mL into 10 mL Schering bottle under sterile conditions and finally freeze-dried to have 10 mg compound IV for each bottle.

What is claimed is:

1. A dimethylamine 4-O-acetyl *inula lineariifolia* lactone A compound represented by compound I:

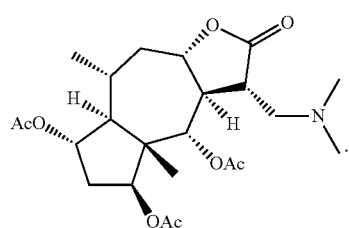

I

2. A pharmaceutically acceptable salt of a dimethylamine 4-O-acetyl *inula lineariifolia* lactone A compound, represented by compound II:

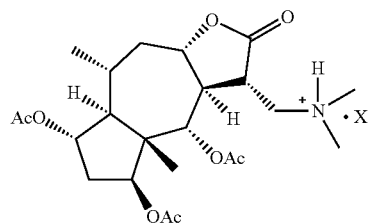

II wherein, the pharmaceutically acceptable salt of the dimethylamine 4-O-acetyl *inula lineariifolia* lactone A compound is synthesized by dimethylamine 4-O-acetyl *inula lineariifolia* lactone A and acids (HX).

3. The pharmaceutically acceptable salt of the dimethylamine 4-O-acetyl *inula lineariifolia* lactone A compound of claim 2, wherein the acids (HX) are hydrochloric acid (HCl), sulfuric acid ($H_2SO_4$), hydrofluoric acid (HF), hydrobromic acid (HBr), hydroiodic acid (HI), Phosphoric acid ($H_3PO_4$), sulfurous acid ($H_2SO_3$), nitric acid ($HNO_3$), carbonic acid ($H_2CO_3$), boric acid ($H_3BO_3$), seleninic acid ($H_2SeO_3$), phosphomolybdic acid ($H_3PO_4 \cdot 12MoO_3$), phosphorous acid ($H_3PO_3$), citric acid, maleic acid, D-malic acid, L-malic acid, DL-malic acid, D-lactic acid, L-lactic acid, DL-lactic acid, oxalic acid, sulphonic acid, benzene sulfonic acid, substituted benzene sulfonic acids, 1-naphthalenesulfonic acid, 2-naphthalenesulfonic acid, phthalic acid, tartaric acid, propandioic acid, succinic acid, fumaric acid, orotic acid, benzoic acid or substituted benzoic acids.

4. The pharmaceutically acceptable salt of the dimethylamine 4-O-acetyl *inula lineariifolia* lactone A compound of claim 2, which comprises dimethylamine 4-O-acetyl *inula lineariifolia* lactone A hydrochloride (compound III), dimethylamine 4-O-acetyl *inula lineariifolia* lactone A fumarate (compound IV), dimethylamine 4-O-acetyl *inula lineariifolia* lactone A nitrate (compound V), dimethylamine 4-O-acetyl *inula lineariifolia* lactone A hydrobromate (compound VI), dimethylamine 4-O-acetyl *inula lineariifolia* lactone A sulfurate (compound VII), dimethylamine 4-O-acetyl *inula lineariifolia* lactone A orotate (compound VIII), dimethylamine 4-O-acetyl *inula lineariifolia* lactone A citrate (compound IX), dimethylamine 4-O-acetyl *inula lineariifolia* lactone A p-toluenesulfonate (compound X) or dimethylamine 4-O-acetyl *inula lineariifolia* lactone A succinate (compound XI), structures of which are shown below:

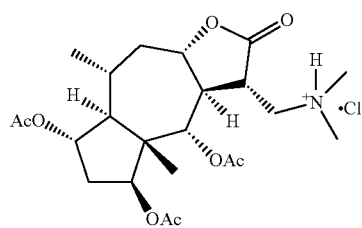

III

IV

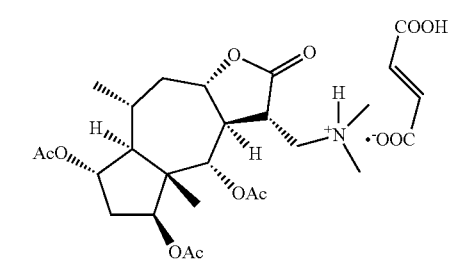

V

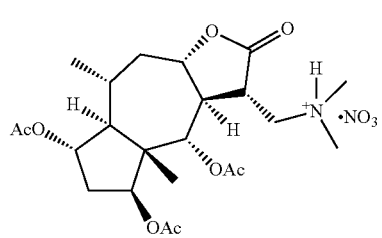

VI

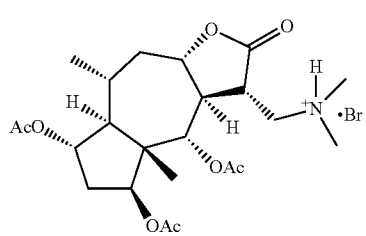

VII

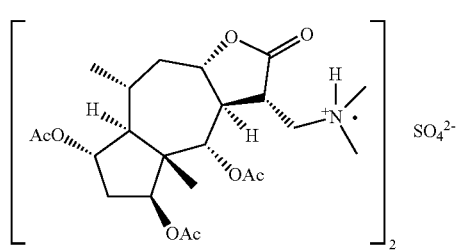

VIII

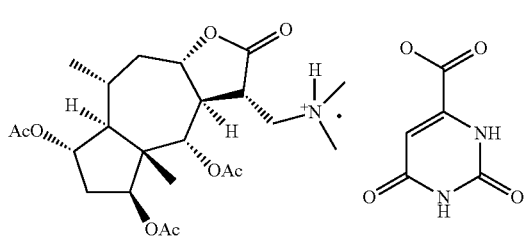

IX

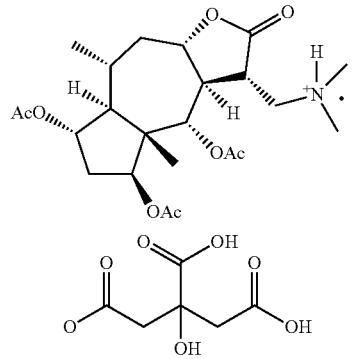

X

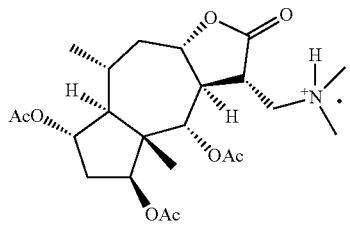

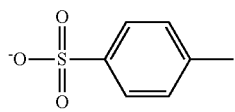

XI

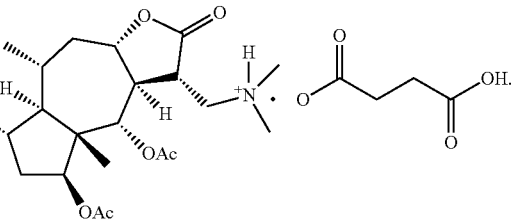

5. The pharmaceutically acceptable salt of the dimethylamine 4-O-acetyl *inula lineariifolia* lactone A compound of claim 4, which comprises dimethylamine 4-O-acetyl *inula lineariifolia* lactone A hydrochloride (compound III) or dimethylamine 4-O-acetyl *inula lineariifolia* lactone A fumarate (compound IV).

6. A preparation method of a dimethylamine 4-O-acetyl *inula lineariifolia* lactone A compound and its pharmaceutically acceptable salt, comprising the following steps of:

(I) preparing the dimethylamine 4-O-acetyl *inula lineariifolia* lactone A compound, comprising the following steps of:

(1) adding an organic solvent to dissolve *inula lineariifolia* lactone A, a base and acetic anhydride (Ac$_2$O) in a reaction container, stirring at 0-50° C. for 12-24 hours until the reaction material is consumed completely and then quenched by water, and retaining an organic layer;

(2) extracting the organic layer with water several times to purify a reaction product 4-O-acetyl *inula lineariifolia* lactone A in the organic layer, discarding an aqueous layer, washing the organic layer with saturated brine, drying with anhydrous sodium sulfate (Na$_2$SO$_4$), and concentrating to 1/10-1/20 of an original volume under reduced pressure 0.01-0.1 MPa at 20-80° C.;

(3) purifying a concentrated solution by silica-gel column chromatography with gradient elution using petroleum ether (PE)/ethyl acetate (EA) 15:1-5:1 to obtain 4-O-acetyl *inula lineariifolia* lactone A;

its reaction equation being shown below:

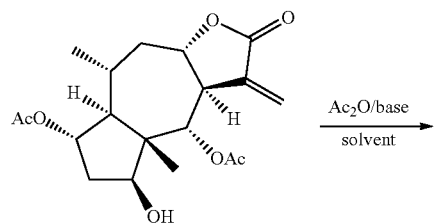

Inula lineariifolia lactone A

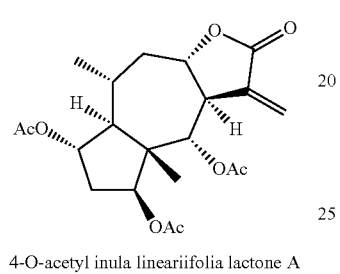

4-O-acetyl inula lineariifolia lactone A (4) adding an organic solvent to dissolve the 4-O-acetyl inula lineariifolia lactone A and dimethylamine hydrochloride ($CH_3NHCH_3 \cdot HCl$) in a reaction container disposed in a cooling tank at −20 to 0° C., slowly adding a base, then slowly increasing a temperature of the reaction mixture to room temperature 25-30° C., and stirring for 2-12 hours until the reaction material is consumed completely, evaporating the solvent under reduced pressure 0.01-0.1 MPa at 20-80° C. to obtain a crude product, then adding an organic reagent to dissolve the crude product, extracting with water, discarding an aqueous layer, repeating the same procedure to purify a reaction product dimethylamino-4-O-acetyl inula lineariifolia lactone A in an organic layer, washing the organic layer with saturated brine, drying with anhydrous sodium sulfate ($Na_2SO_4$), performing silica-gel column chromatography with gradient elution using PE/EA 15:1-1:1, monitored by TLC, collecting eluent including the dimethylamino-4-O-acetyl inula lineariifolia lactone A compound (compound I), evaporating the solvent under reduced pressure 0.01-0.1 MPa at 20-80° C. to obtain the compound I;

its reaction equation being shown below:

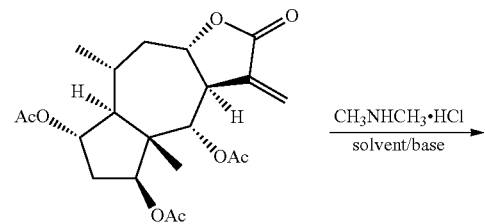

4-O-acetyl inula lineariifolia lactone A

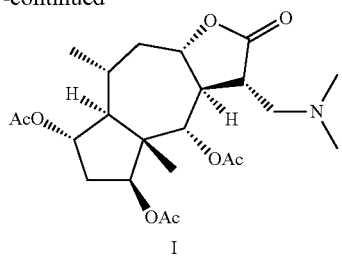

I (II) preparing the salt of dimethylamino-4-O-acetyl inula lineariifolia lactone A compound: 1.0eq of compound I being dissolved in a solvent, and being stirred with 1.0-1.5eq of an acid (HX) at 0-50° C. for 2-24 hours, concentrating under reduced pressure 0.01-0.1 MPa at 20-80° C. to obtaining the salt of compound II, its reaction equation being shown below:

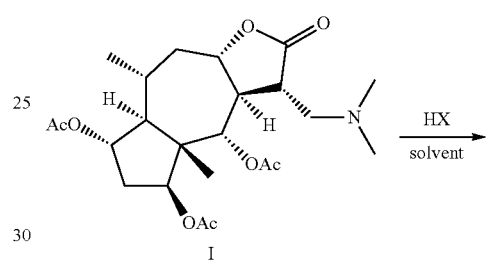

I

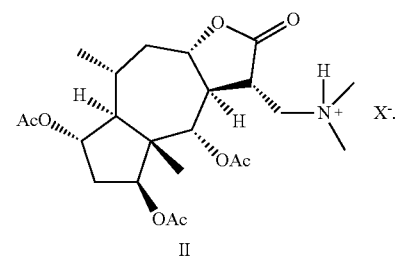

II

7. The preparation method of the dimethylamine 4-O-acetyl inula lineariifolia lactone A compound and its pharmaceutically acceptable salt of claim 6, wherein:
  a ratio of the inula lineariifolia lactone A:the base:acetic anhydride ($Ac_2O$) are 1.0eq:1.0-2.0eq:1.0-2.0eq in the step (I) of preparation of the compound I;
  the organic reagent is a reagent insoluble in water comprising one of ethyl acetate, dichloromethane, chloroform, tetrachloromethane, ethyl ether, petroleum ether, n-butyl alcohol, benzene, methylbenzene and tetrahydrofuran, or a mixture thereof;
  the base is a low molecular weight trialkyl-substituted amine comprising trimethylamine, triethylamine, tripropylamine or tributylamine, pyridine or substituted pyridine, or dimethylpyridine;
  a ratio of the 4-O-acetyl inula lineariifolia lactone A:dimethylamine hydrochloride:the base is 1.0eq:1.0-2.0eq:1.0-2.0eq in the step (4);
  the organic solvent is a low molecular weight fatty alcohol comprising one of methanol, ethanol, propanol, isopropanol, dichloromethane, chloroform, tetrachloromethane, ethyl ether, petroleum ether and ethyl acetate, or a mixture thereof;
  the organic reagent is a reagent insoluble in water comprising one of ethyl acetate, dichloromethane, chloroform, tetrachloromethane, ethyl ether, petroleum ether, n-butyl alcohol, benzene, methylbenzene and tetrahydrofuran, or a mixture thereof;

the base is a low molecular weight trialkyl-substituted amine, pyridine or substituted pyridine, the alkyl group is methyl, ethyl, propyl or butyl, or triethylamine.

8. The preparation methods of dimethylamine 4-O-acetyl *inula lineariifolia* lactone A compound and its pharmaceutically acceptable salt of claim 6, wherein a ratio of the dimethy-4-O-acetyl *inula lineariifolia* lactone A compound (compound I) and the acid (HX) is 1.0eq: 1.0-1.5eq in the step (II) of preparation of the salt of the compound I;

the acid (HX) is hydrochloric acid (HCl), sulfuric acid ($H_2SO_4$), hydrofluoric acid (HF), hydrobromic acid (HBr), hydroiodic acid (HI), phosphoric acid ($H_3PO_4$), sulfurous acid ($H_2SO_3$), nitric acid ($HNO_3$), carbonic acid ($H_2CO_3$), boric acid ($H_3BO_3$), seleninic acid ($H_2SeO_3$), phosphomolybdic acid ($H_3PO_4.12MoO_3$), phosphorous acid ($H_3PO_3$), citric acid, maleic acid, D-malic acid, L-malic acid, DL-malic acid, D-lactic acid, L-lactic acid, DL-lactic acid, oxalic acid, sulphonic acid, benzene sulfonic acid, substituted benzene sulfonic acids, 1-naphthalenesulfonic acid, 2-naphthalenesulfonic acid, phthalic acid, tartaric acid, propandioic acid, butanedioic acid, fumaric acid, citric acid, orotic acid, benzoic acid, substituted benzoic acids, hydrochloric acid, fumaric acid, nitric acid, hydrobromic acid, sulfuric acid, orotic acid, citric acid, p-toluenesulfonic acid, butanedioic acid;

the solvent is a low molecular weight fatty alcohol comprising one of methanol, ethanol, propanol, isopropanol, dichloromethane, chloroform, tetrachloromethane, ethyl ether, petroleum ether and ethyl acetate, or a mixture thereof, and preferably is ethanol.

9. A crystal form A of dimethylamino-4-O-acetyl *inula lineariifolia* lactone A fumarate (compound IV), having the following characteristics:

a powder X-ray diffraction (PXRD) of the crystal form A with values of 2θ, d and relative intensity listed in the following table:

| 2θ | d (Å) | I (Height) % |
|---|---|---|
| 8.101 | 10.9048 | 5.6 |
| 9.72 | 9.092 | 66.5 |
| 10.22 | 8.6484 | 77.4 |
| 11.62 | 7.6093 | 37.7 |
| 12.381 | 7.1435 | 6.8 |
| 14.86 | 5.9568 | 11.7 |
| 15.84 | 5.5903 | 37.8 |
| 16.28 | 5.4402 | 32.3 |
| 17.499 | 5.0639 | 18.4 |
| 19.56 | 4.5347 | 70.2 |
| 20.64 | 4.2998 | 100 |
| 21.081 | 4.2108 | 21.9 |
| 21.819 | 4.07 | 42.6 |
| 23.381 | 3.8016 | 72.4 |
| 24.12 | 3.6866 | 4.3 |
| 24.939 | 3.5674 | 41.5 |
| 25.281 | 3.52 | 40.3 |
| 26.34 | 3.3808 | 7.5 |
| 26.901 | 3.3115 | 11.4 |
| 27.581 | 3.2315 | 16.4 |
| 29.436 | 3.0318 | 4.8 |
| 30.021 | 2.9741 | 7.2 |
| 31.001 | 2.8823 | 23.4 |
| 32.038 | 2.7913 | 6.9 |
| 32.498 | 2.7528 | 2.3 |
| 32.922 | 2.7183 | 3.2 |
| 33.302 | 2.6882 | 10.1 |
| 34.361 | 2.6077 | 3.2 |
| 35.879 | 2.5008 | 5.9 |
| 37.34 | 2.4062 | 5.5 |
| 38.998 | 2.3077 | 4.3 |
| 40.121 | 2.2456 | 7.5 |
| 41.8 | 2.1592 | 7.4 | wherein a PXRD pattern of the crystal form A is shown in FIG. 1, and the structure of compound IV is shown below:

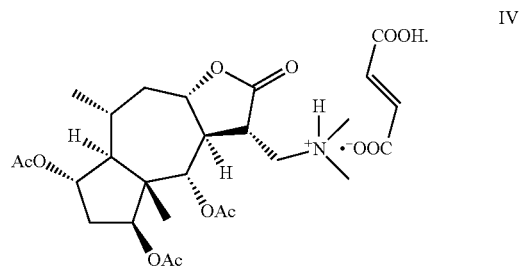

IV

10. A preparation method of a crystal form A of dimethylamine 4-O-acetyl *inula lineariifolia* lactone A fumarate (compound IV), wherein the compound IV is dissolved in 2 to 5 folds ethyl acetate, adding 2 to 5 folds n-hexane and stirring until crystals are deposited, filtrating the crystals and drying under reduced pressure to vacuum at 25-40° C. to obtain the crystal form A of the compound IV, wherein the structure of compound IV is shown below:

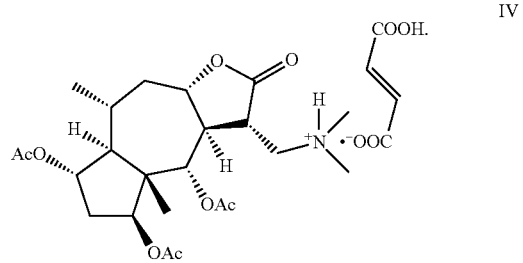

IV

11. A crystal form D of dimethylamino-4-O-acetyl *inula lineariifolia* lactone A fumarate (compound IV), having the following characteristics:

a powder X-ray diffraction (PXRD) of the crystal form D with values of 2θ, d and relative intensity listed in the following table:

| 2θ | d (Å) | I (Height) % |
|---|---|---|
| 8.6 | 10.2736 | 100 |
| 9.777 | 9.0388 | 30.8 |
| 10.659 | 8.2929 | 21.5 |
| 11.102 | 7.9633 | 3.7 |
| 13.021 | 6.7936 | 10 |
| 14.64 | 6.0457 | 60.5 |
| 15.039 | 5.8861 | 24 |
| 16.24 | 5.4535 | 35.4 |
| 16.879 | 5.2484 | 20 |
| 17.298 | 5.1221 | 4.7 |

-continued

Figure 2:
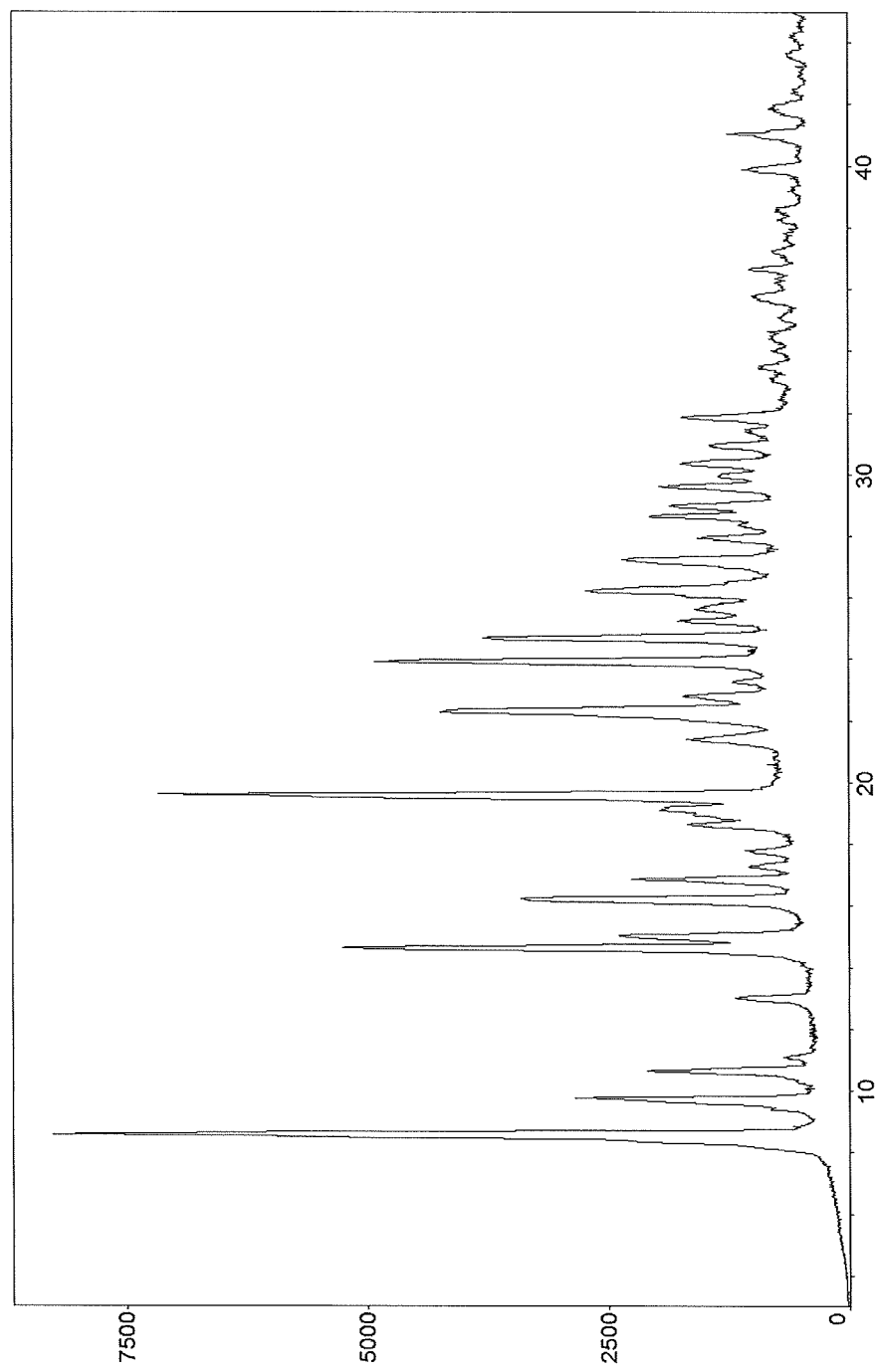
FIG. 2 is a PXRD pattern of compound IV in crystal form D.

| 2θ | d (Å) | I (Height) % |
|---|---|---|
| 17.8 | 4.979 | 5.5 |
| 18.659 | 4.7514 | 13.4 |
| 19.12 | 4.638 | 16.1 |
| 19.619 | 4.5211 | 78.2 |
| 21.418 | 4.1453 | 10.6 |
| 22.3 | 3.9832 | 42.2 |
| 22.801 | 3.8969 | 10.3 |
| 23.266 | 3.82 | 3.8 |
| 23.939 | 3.7141 | 50.4 |
| 24.699 | 3.6015 | 35.6 |
| 25.259 | 3.5229 | 9.7 |
| 25.639 | 3.4716 | 8.3 |
| 26.24 | 3.3935 | 20.8 |
| 27.24 | 3.2711 | 19 |
| 27.961 | 3.1883 | 8.8 |
| 28.379 | 3.1423 | 4.2 |
| 28.659 | 3.1123 | 15.7 |
| 28.981 | 3.0784 | 12.7 |
| 29.62 | 3.0135 | 14.2 |
| 29.941 | 2.9818 | 6.5 |
| 30.36 | 2.9416 | 11.2 |
| 30.996 | 2.8827 | 7.4 |
| 31.478 | 2.8397 | 4 |
| 31.861 | 2.8064 | 11.5 |
| 35.799 | 2.5062 | 4.6 |
| 36.646 | 2.4502 | 4.7 |
| 39.882 | 2.2586 | 7.3 |
| 41.057 | 2.1966 | 9.5 |
| 41.9 | 2.1543 | 4.5 | wherein a PXRD pattern of the crystal form D is shown in FIG. 2, and the structure of compound IV is shown below:

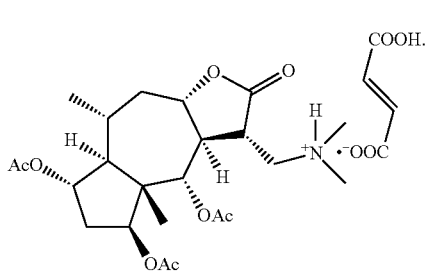

12. A preparation method of a crystal form D of dimethylamine 4-O-acetyl *inula lineariifolia* lactone A fumarate (compound IV), wherein the compound IV is put into methyl tert-butyl ether (MTBE) containing 0.2% water, then stirring for 2-5 hours, removing a solvent by filtration, drying at 40-60° C. under reduced pressure 0.03-0.1 MPa to vacuum for 4-24 hours to obtain the crystal form D of the compound IV, wherein the structure of compound IV is shown below:

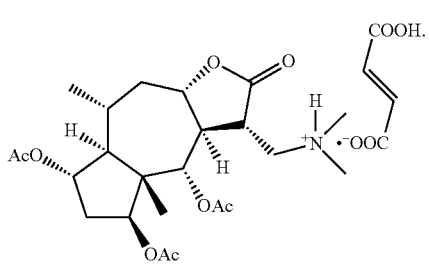

Figure 3:
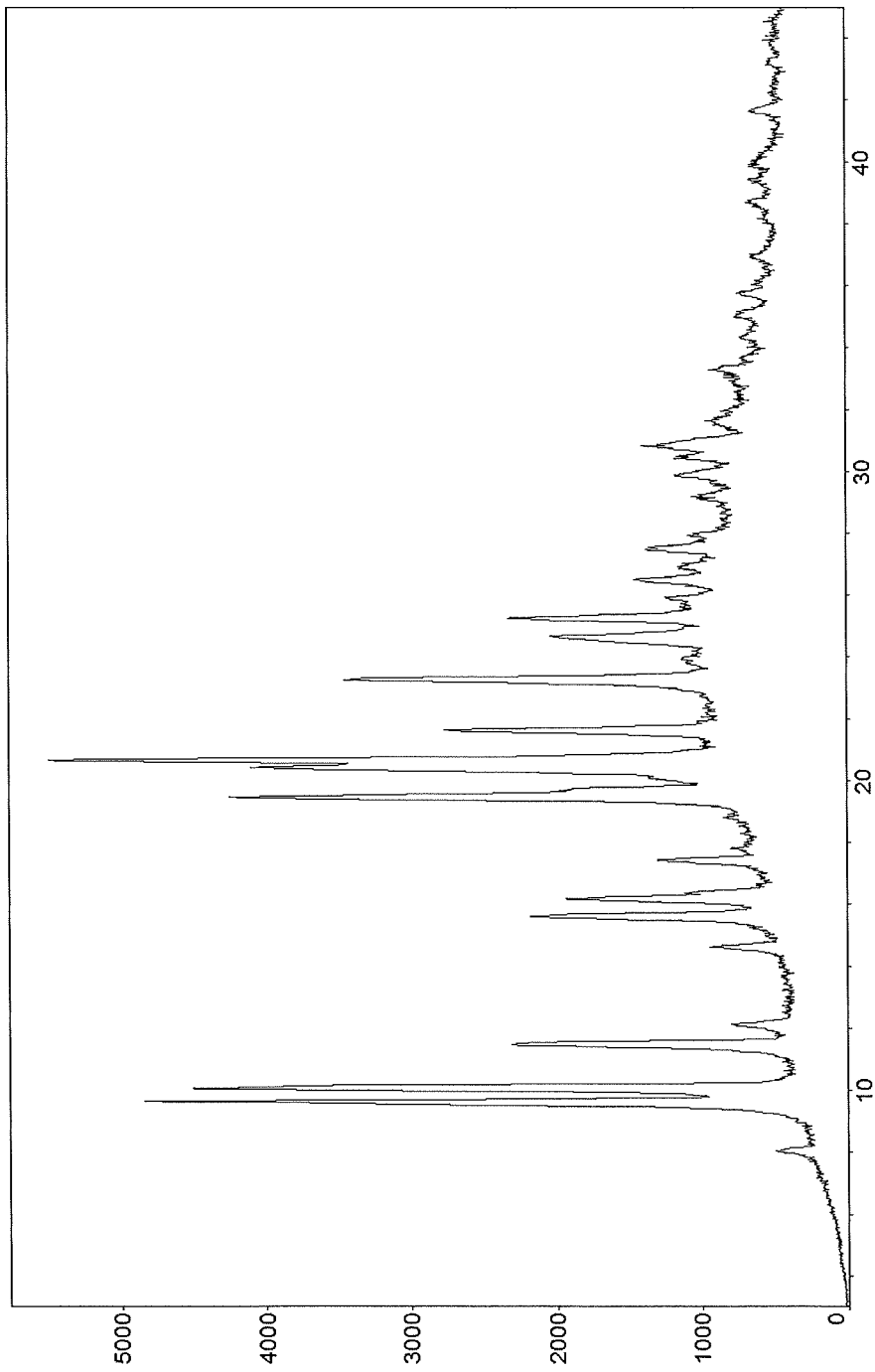
FIG. 3 is a PXRD pattern of compound IV in crystal form F.

13. A crystal form F of dimethylamino-4-O-acetyl *inula lineariifolia* lactone A fumarate (compound IV), having the following characteristics:

a powder X-ray diffraction (PXRD) of the crystal form F with values of 2θ, d and relative intensity listed in the following table:

| 2θ | d (Å) | I (Height) % |
|---|---|---|
| 8.06 | 10.9609 | 5.4 |
| 9.659 | 9.1493 | 100 |
| 10.08 | 8.7682 | 91.7 |
| 11.5 | 7.6884 | 42.3 |
| 12.139 | 7.2851 | 7.7 |
| 14.642 | 6.0449 | 9.8 |
| 15.639 | 5.6616 | 35.8 |
| 16.2 | 5.4669 | 30 |
| 17.441 | 5.0806 | 15.1 |
| 19.48 | 4.5531 | 73 |
| 20.44 | 4.3413 | 68.1 |
| 20.679 | 4.2916 | 99.4 |
| 21.639 | 4.1034 | 40.1 |
| 23.28 | 3.8177 | 54.9 |
| 24.68 | 3.6043 | 21.8 |
| 25.261 | 3.5227 | 29.8 |
| 25.938 | 3.4322 | 6 |
| 26.52 | 3.3582 | 11.3 |
| 26.938 | 3.3071 | 4.3 |
| 27.482 | 3.2428 | 9.8 |
| 27.958 | 3.1887 | 4.4 |
| 29.201 | 3.0557 | 5.1 |
| 29.918 | 2.9841 | 7.3 |
| 30.442 | 2.9339 | 8.6 |
| 30.839 | 2.8971 | 13.4 |
| 31.657 | 2.824 | 4.7 |
| 33.3 | 2.6884 | 6.2 |
| 34.341 | 2.6092 | 2.6 |
| 35.02 | 2.5601 | 4.1 |
| 35.778 | 2.5076 | 4.3 | wherein a PXRD pattern of the crystal form F is shown in FIG. 3, and the structure of compound IV is shown below:

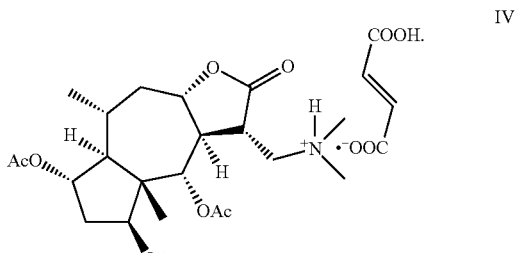

14. A preparation method of a crystal form F of dimethylamine 4-O-acetyl *inula lineariifolia* lactone A fumarate (compound IV), wherein the compound IV is dissolved in 1 to 2 folds methanol, adding 2 to 5 folds ether and stirring until crystals are deposited, filtrating the crystals and drying at 25-40° C. under reduced pressure 0.03-0.1 MPa to vacuum for 2-24 hours to obtain the crystal form F of the compound IV, wherein the structure of compound IV is shown below:

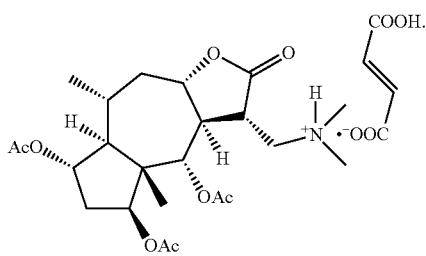

Figure 4:
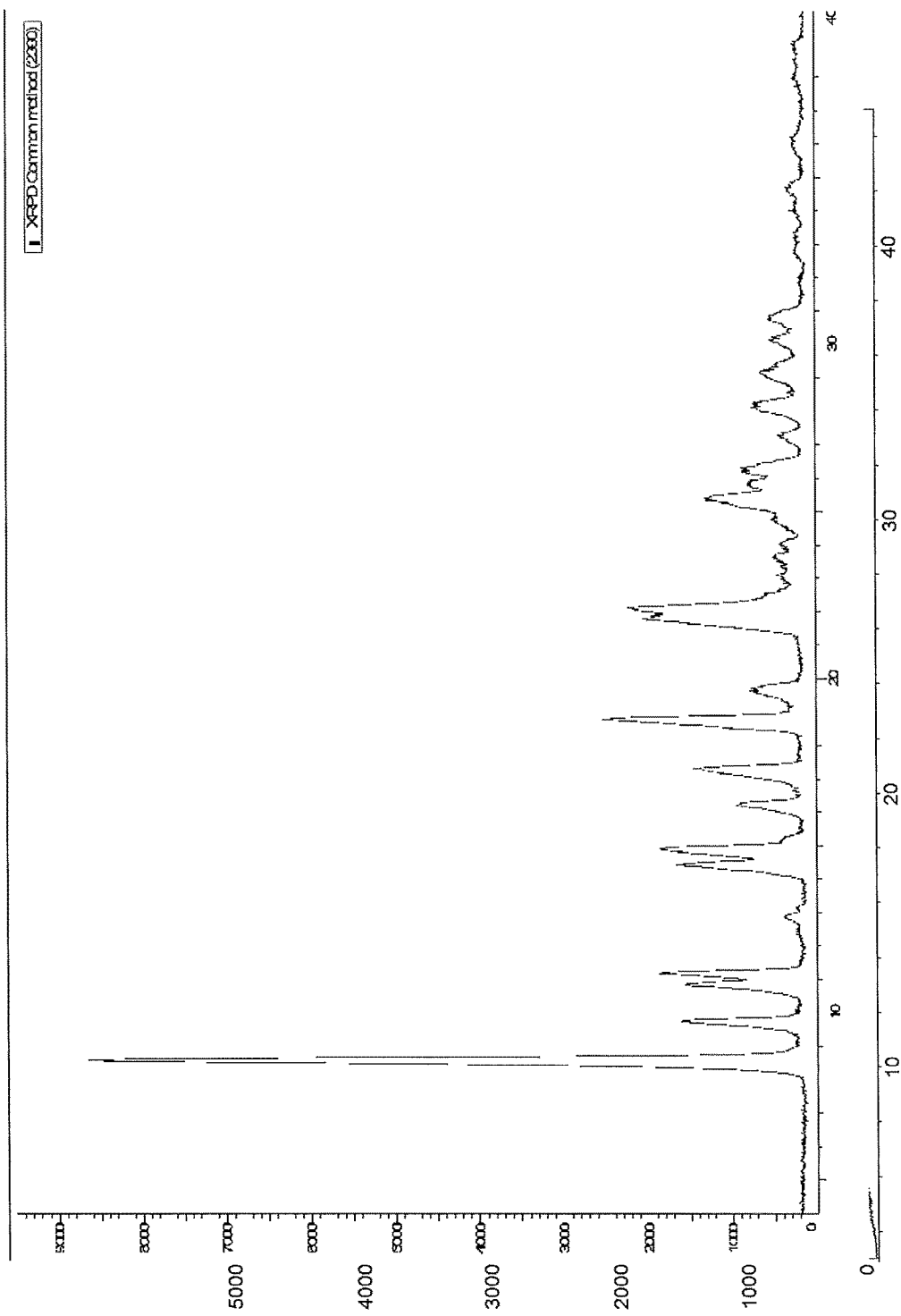
FIG. 4 is a PXRD pattern of compound IV in crystal form G.

15. A crystal form G of dimethylamino-4-O-acetyl *inula lineariifolia* lactone A fumarate (compound IV), having the following characteristics:

a powder X-ray diffraction (PXRD) of the crystal form G with values of 2θ, d and relative intensity listed in the following table:

| 2θ | d (Å) | I (Height) % |
|---|---|---|
| 8.567 | 10.31279 | 100.0 |
| 7.931 | 9.08148 | 17.0 |
| 10.849 | 8.14803 | 16.7 |
| 11.163 | 7.92006 | 193.4 |
| 12.452 | 7.10295 | 0.8 |
| 12.865 | 6.87584 | 2.7 |
| 13.115 | 6.74542 | 1.0 |
| 14.413 | 6.14053 | 17.9 |
| 14.869 | 5.95311 | 20.0 |
| 15.128 | 5.85184 | 3.2 |
| 16.225 | 5.45870 | 9.0 |
| 17.268 | 5.13128 | 13.8 |
| 18.761 | 4.72601 | 26.8 |
| 19.661 | 4.51181 | 6.0 |
| 21.872 | 4.06030 | 20.3 |
| 22.059 | 4.02635 | 22.8 |
| 23.059 | 3.85401 | 1.9 |
| 23.631 | 3.73193 | 3.0 |
| 24.014 | 3.70281 | 2.1 |
| 24.809 | 3.58595 | 3.0 |
| 25.401 | 3.50361 | 13.1 |
| 25.830 | 3.44652 | 6.9 |
| 26.245 | 3.39285 | 7.6 |
| 27.267 | 3.26804 | 2.5 |
| 28.160 | 3.16634 | 5.4 |
| 29.131 | 3.06300 | 5.0 |
| 30.138 | 2.96286 | 3.8 |
| 30.797 | 2.90094 | 4.1 |
| 32.824 | 2.72631 | 1.0 |
| 33.257 | 2.69179 | 0.6 |
| 34.654 | 2.58642 | 1.6 |
| 36.124 | 2.48445 | 1.2 |
| 38.027 | 2.36438 | 1.0 |
| 38.503 | 2.33628 | 1.0 |
| 38.942 | 2.31091 | 1.0 | wherein a PXRD pattern of the crystal form G is shown in FIG. 4, and the structure of compound IV is shown below:

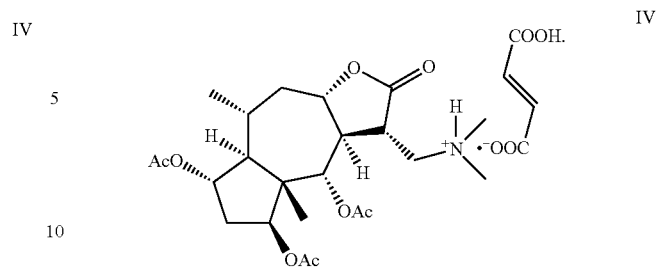

16. A preparation method of a crystal form G of dimethylamine 4-O-acetyl *inula lineariifolia* lactone A fumarate (compound IV), wherein compound I is dissolved in 2 folds ethanol, adding with equivalent fumaric acid while stirring, continuously stirring for 0.5-2 hours, adding with 1 to 2 folds MTBE to separate out crystals, filtrating the crystals, drip washing by MTBE, drying at 25-40° C. in vacuum to obtain the crystal form G of the compound IV, wherein the structure of compound IV is shown below:

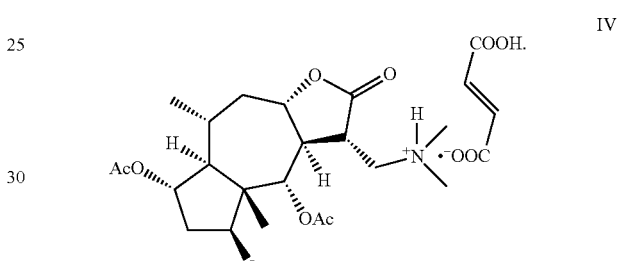

17. A method for treating multiple sclerosis by administering dimethylamino-4-O-acetyl *inula lineariifolia* lactone A compound (compound D or its pharmaceutically acceptable salt (compound II), wherein the structures of said compounds are shown below:

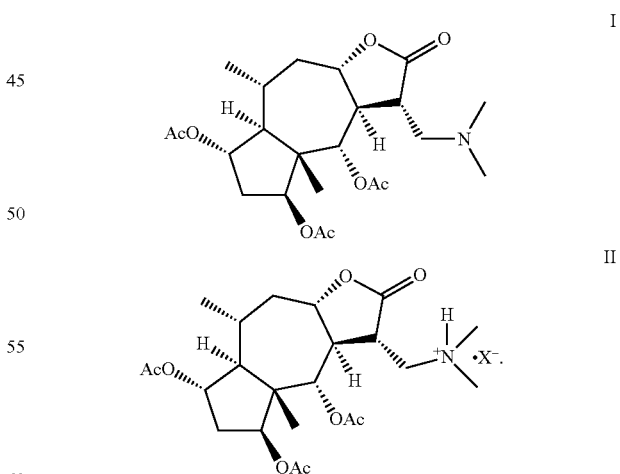

18. A method for treating multiple sclerosis by administering a pharmaceutical composition made of a dimethylamino-4-O-acetyl *inula lineariifolia* lactone A compound (compound I) or its pharmaceutically acceptable salt (compound II) combined with a medicinal carrier, wherein the structures of said compounds are shown below:

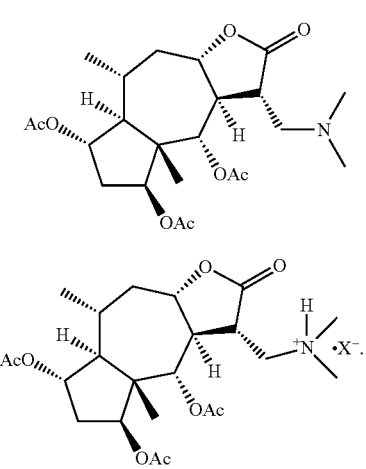
I
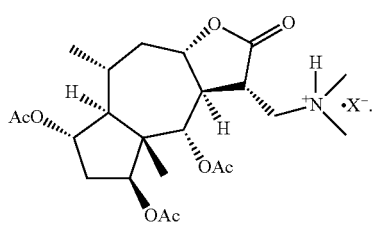
II
19. The method of claim 18, wherein the pharmaceutical composition is tablets, dispersible tablets, lozenge, mouth collapse tablets, retard tablets, capsules, soft capsules, dropping pills, granules, injections, powder injections or aerosols.
* * * * *